(12) United States Patent
Nguyen et al.

(10) Patent No.: US 9,561,095 B1
(45) Date of Patent: *Feb. 7, 2017

(54) BODY AUGMENTATION DEVICE

(71) Applicants: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(72) Inventors: Phi Nguyen, Houston, TX (US); Loc Phan, San Jose, CA (US); Bao Tran, Saratoga, CA (US); Thuan Nguyen, Houston, CA (US); Duy Bui, Ha Noi (VN)

(*) Notice: Subject to any disclaimer, the term of this patent is extended or adjusted under 35 U.S.C. 154(b) by 0 days.

This patent is subject to a terminal disclaimer.

(21) Appl. No.: 14/881,028

(22) Filed: Oct. 12, 2015

(51) Int. Cl.
| | |
|---|---|
| A61F 2/02 | (2006.01) |
| A61F 2/12 | (2006.01) |
| A61M 5/172 | (2006.01) |
| A61L 27/20 | (2006.01) |
| A61L 27/16 | (2006.01) |
| A61L 27/54 | (2006.01) |
| A61L 27/52 | (2006.01) |
| A61K 31/496 | (2006.01) |
| A61K 9/00 | (2006.01) |
| A61B 5/103 | (2006.01) |
| A61M 5/20 | (2006.01) |

(52) U.S. Cl.
CPC .......... *A61F 2/02* (2013.01); *A61B 5/103* (2013.01); *A61F 2/12* (2013.01); *A61K 9/0024* (2013.01); *A61K 31/496* (2013.01); *A61L 27/16* (2013.01); *A61L 27/20* (2013.01); *A61L 27/52* (2013.01); *A61L 27/54* (2013.01); *A61M 5/1723* (2013.01); *A61M 5/20* (2013.01); *A61L 2300/21* (2013.01); *A61L 2300/41* (2013.01); *A61L 2300/602* (2013.01); *A61L 2400/06* (2013.01)

(58) Field of Classification Search
CPC ...... A61M 5/20; A61M 5/1723; A61M 31/00; A61F 2/02; A61F 2/12; A61B 5/1037
See application file for complete search history.

(56) References Cited

U.S. PATENT DOCUMENTS

| | | |
|---|---|---|
| 4,531,244 A | 7/1985 | Hamas |
| 4,538,920 A * | 9/1985 | Drake .................. A61C 5/064 222/137 |
| 4,648,880 A | 3/1987 | Brauman |
| 4,801,539 A | 1/1989 | Akasaka |
| 4,955,907 A | 9/1990 | Ledergerber |
| 5,219,360 A | 6/1993 | Georgiade |
| 5,891,701 A | 4/1999 | Sloma |
| 6,231,605 B1 | 5/2001 | Ku |

(Continued)

OTHER PUBLICATIONS

Hassan et al, Structure and Applications of Poly(vinyl alcohol) Hydrogels Produced by Conventional Crosslinking or by Freezing/Thawing Methods, Advances in Polymer Science vol. 153, 2000.

(Continued)

*Primary Examiner* — Bhisma Mehta
*Assistant Examiner* — Jenna Zhang
(74) *Attorney, Agent, or Firm* — Tran & Associates

(57) ABSTRACT

Systems and methods are disclosed for filler injection. The apparatus includes a processor; a body sensor to provide body patient data to the processor; and an injector to inject a filler into a patient.

19 Claims, 15 Drawing Sheets

---

Capture a 3D model of a patient body portion using one or more cameras (70)

Model shaping and size change in the body portion due to an implant (72)

Iteratively changing body shapes or sizes until the patient is satisfied with a desired shape or size (74)

Control an automatic injector to deliver the implant in the patient (76)

Monitor injection into patient and providing feedback if needed to achieve the desired shape and size (78)

(56) References Cited

U.S. PATENT DOCUMENTS

| | | | |
|---|---|---|---|
| 6,248,405 B1 | 6/2001 | Kastl | |
| 6,546,279 B1 * | 4/2003 | Bova | A61B 8/0833 |
| | | | 600/410 |
| 6,881,226 B2 | 4/2005 | Corbitt | |
| 6,981,988 B1 | 1/2006 | Kinsley | |
| 7,137,995 B2 * | 11/2006 | Studin | A61F 2/12 |
| | | | 604/181 |
| 7,235,592 B2 | 6/2007 | Muratoglu | |
| 7,491,709 B2 | 2/2009 | Carey | |
| 7,587,075 B1 | 9/2009 | Stefan | |
| 2004/0092653 A1 | 5/2004 | Ruberti | |
| 2007/0212385 A1 * | 9/2007 | David | A61K 8/02 |
| | | | 424/422 |
| 2008/0171706 A1 * | 7/2008 | Berglund | A61K 31/70 |
| | | | 514/23 |
| 2008/0228268 A1 | 9/2008 | Shannon | |
| 2009/0181104 A1 * | 7/2009 | Rigotti | A61F 2/12 |
| | | | 424/574 |
| 2009/0240200 A1 * | 9/2009 | Heneveld | A61F 2/0059 |
| | | | 604/121 |
| 2009/0299328 A1 * | 12/2009 | Mudd | A61M 5/20 |
| | | | 604/506 |
| 2011/0142936 A1 * | 6/2011 | Campbell | A61L 27/50 |
| | | | 424/484 |
| 2012/0208890 A1 | 8/2012 | Gousse | |

OTHER PUBLICATIONS

Mabrouk, Effect of ciprofloxacin incorporation in PVA and PVA bioactive glass composite scaffolds, Ceramics International, Aug. 12, 2013.

Mishra, Radiation induced crosslinking effect on semi-interpenetrating polymer networks of poly(vinyl alcohol), eXPRESS Polymer Letters vol. 1, No. 7 (2007) 407-415.

* cited by examiner

| |
|---|
| Capture 3D model of patient (50) |
| Isolate breast or butt region (52) |
| Model shape and size of breast or butt increase due to implant (54) |
| Morph or project the shape/size of breast or butt increase onto the 3D model of patient (56) |
| Allow user to iterative change balloon shapes/sizes until satisfied with new shape (58) |
| Allow user to select from a library of wardrobes to provide realistic simulation (60) |
| Monitor injection into patient and provide feedback to professionals on additional injections if needed to achieve desired shape and size (62) |

FIG. 2A

Mix HA and PVA in water at 45C for 3hrs (10)

Freeze at -20C for 20hrs (12)

Sit at Room Temp for 8hrs (14)

Sterilize and Package (16)

FIG. 7A

Mix HA and PVA in water (50)

↓

Sterilize Mixture (52)

↓

Perform Multiple Freeze/Thaw Cycles (54)

↓

Thaw at Room Temperature and then Package (56)

FIG. 7C

Mix HA and PVA in water at 45C for 3hrs (70)

Sterilize Mixture (72)

Multiple Freeze/Thaw Cycles (74)

Sit at Room Temp for 8hrs (76)

Package (78)

FIG. 7D

Mix HA and PVA in water (80)

Sterilize Mixture and cross-linking with eBeam (82)

Optionally perform one or more Freeze/Thaw Cycles (84)

Package (86)

FIG. 7E

```
┌─────────────────────────────────┐
│   Mix HA, PVA and anti-         │
│ inflammatory agent in water at  │
│      45C for 3hrs (130)         │
└─────────────────────────────────┘
                 ┆
┌─────────────────────────────────┐
│     Sterilize Mixture (132)     │
└─────────────────────────────────┘
                 ┆
┌─────────────────────────────────┐
│   Freeze at -20C for 20hrs (134)│
└─────────────────────────────────┘
                 ┆
┌─────────────────────────────────┐
│   Sit at Room Temp for 8hrs (136)│
└─────────────────────────────────┘
                 ┆
┌─────────────────────────────────┐
│         Package (138)           │
└─────────────────────────────────┘
```

FIG. 11

BODY AUGMENTATION DEVICE

This application is a continuation-in-part of application Ser. No. 14/255,952 filed on Apr. 17, 2014 and application Ser. No. 14/255,967 filed on Apr. 12, 2013, both of which claiming priority to Provisional Application Ser. 61/722,221 filed Nov. 4, 2012, and PCT Application Serial PCT/VN2013/000001 filed Apr. 12, 2013, PCT/VN2013/000002 filed Apr. 12, 2013, PCT/VN2013/000003 filed on Apr. 12, 2013, PCT/VN2013/000004 filed Apr. 12, 2013, and PCT/VN2012/000008 filed Dec. 17, 2012, the contents of which are incorporated by reference.

BACKGROUND OF INVENTION

This present invention relates to soft tissue body augmentation, for example the face, breast, buttock, and other body parts.

Augmenting or changing the shape of the soft tissue of the human body has been done previously in medicine by harvesting donor tissue from one part of the body then processing and introducing it to another desired part of the body or by using implants. The donor tissue is usually adipose or fatty tissue or muscle and the harvesting of the donor tissue is time consuming and often leaves an unwanted defect and scars from the harvested site. The procedure time is lengthened with the harvesting and processing of the tissue and adds greatly to the cost of the procedure and the recovery time is also prolonged. The donor tissue will then have to be placed in the desired area usually through surgical means which can be lengthy and costly and usually laves a large scar as in the case of the breast or buttocks (butts).

Reconstruction of the human breast or butt involves introducing a fixed or changeable-volume sac-like silicone rubber structure into a body cavity surgically created to receive such an implant. The implants and coverings therefore are described, by way of illustration and not by limitation, in: Braumann U.S. Pat. No. 4,648,880; Hamas U.S. Pat. No. 4,531,244; Ledergerber U.S. Pat. No. 4,955,907, Corbitt U.S. Pat. No. 6,881,226, Kinsley U.S. Pat. No. 6,981,988, and Studin U.S. Pat. No. 7,137,995, the contents of which are incorporated by reference.

Known methods of augmentation mammoplasty utilize silicone or saline implants. These methods have been complicated post-operatively by encapsulation of the implants, which can occur to varying degrees. Encapsulation produces a hard area of scar tissue around the implant, resulting in a rigid, abnormally-shaped mound beneath the breast or butt tissue or pectoralis muscle, depending upon the placement of the implant.

The usual skin incision is on the order of 3-8 centimeters in length and is stretched open with retractors to facilitate the introduction of the implant. In various surgical procedures, a breast or butt implant is placed within the surgically formed body cavity for subsequent inflation and/or deflation with a fluid.

In plastic and reconstructive surgery, when a breast or butt implant or tissue expander is placed in the dissected pocket, it is typically filled via a fill connector coupled to fill tubing which is attached to a filling material (e.g. saline solution) source.

There are currently three basic types of fill connectors used to connect the fluid source to the implant, the choice of which often depends on the implant and the particular surgical approach used. The first is a permanent attachment of the fill tubing to the implant. A common means for this attachment is to make a small opening within the body or shell of the implant and insert the tubing securing it by means of connecting materials such as sleeves, patch assemblies, adhesives or vulcanizing compounds.

The other two common connectors are for temporary attachment of the fill tubing to the implant by means of a valve in the implant which seals after the fill tubing is removed. One of these two temporary attachment means is most commonly used with saline-fill breast or butt implant devices that include a diaphragm valve within the shell. The valve has an opening that requires a rigid male implement to be inserted in the opening thus opening the valve and allowing fluid transfer. This male implement is the fill tip end of the fill connector, which has on the opposite end one or more barbs which accept the flexible (e.g. silicone or vinyl) fill tubing. In use, the fill connector and fill tubing attach to the implant normal to the implant surface.

Since breast or butt implants are usually placed into the body through incisions considerably smaller than the implant, it has always been a challenge to introduce them. With greatly increased friction at the interface between the surface of newer texturized implants and the wound margins (body tissue), it has become correspondingly more difficult to introduce these implants. Increased manipulation of both implants and patient tissue often results in trauma to both implants and patient tissue, thereby increasing the risk associated with the procedure both in terms of immediate consequences as well as delayed structural failure and the implications deriving therefrom. Postoperative infection has also been a troublesome consequence of the need to manipulate the implant into place.

In a related art, U.S. Pat. No. 7,491,709 discloses methods of providing long-term minimization of wrinkles or folds in the skin by injecting a bolus of hyaluronic acid deep into the skin. The methods are particularly beneficial for improving the contours of the cheeks, filling folds under the eyes, and providing the visual effect of a chin implant, without requiring the use of surgical procedures.

United States Patent Application 20090240200 discloses a system for inserting a distal end portion of a needle of a medical injector into a skin of a body. An energy source operatively coupled to the medical injector is actuated such that a dermal filler is conveyed from the medical injector into the skin through the distal end portion of the needle. The distal end portion of the needle is moved within the skin during the actuating.

SUMMARY OF THE INVENTION

In one aspect, an apparatus includes a processor; a 3D imaging system coupled to the processor; and an injector to inject a filler into a patient.

In another aspect, a method for body augmentation includes: capturing body patient data using a body sensor communicating with a processor; and placing a filler into a patient using an injector.

In yet another aspect, a method to perform cosmetic enhancements includes capturing a 3D model of a patient body portion using one or more cameras; modeling shape and size change in the body portion due to an implant; iteratively change body shapes or sizes until the patient is satisfied with a desired shape or size; controlling an automatic injector to deliver the implant in the patient; and monitoring injection into patient and providing feedback if needed to achieve the desired shape and size.

Implementations may include on or more of the following. The injector includes a medicament container, an energy source, and one of: a cannula, a blunt tip, or a needle. The processor continuously updates a current shape of breast or butt from a 3D model of the patient to fit to a desired shape. The body sensor comprises a camera to capture patient profile, a contact sensor or a contactless sensor. The injector injects hyaluronic acid (HA), polyvinyl alcohol (PVA), or a combination thereof. The injector injects an anti-inflammatory agent with either hyaluronic acid (HA) or polyvinyl alcohol (PVA) into the patient. The injector injects hyaluronic acid (HA) with polyvinyl alcohol (PVA) to form an HA-PVA hydrogel, and wherein the HA-PVA hydrogel is exposed to an amount of energy effective to crosslink the HA and the PVA. The injector injects hyaluronic acid (HA) with polyvinyl alcohol (PVA) to form an HA-PVA hydrogel; and wherein the HA-PVA hydrogel is exposed to an amount of energy effective to crosslink the HA and the PVA and to sterilize the HA and the PVA. The injector injects polyvinyl alcohol (PVA) cross-linked using one or more freeze-thaw cycles. The injector injects polyvinyl alcohol (PVA) cross-linked using e-beam, X-ray, or gamma ray, or beta particle. The injector injects polyvinyl alcohol (PVA) with an anti-inflammatory agent. The injector injects a multiply cross-linked material with one or more interpenetrating network (IPN) regions each with one or more single cross-linked extensions radiating out from the IPN. The combination of the IPN and the extensions provide one or more of: biodegradation resistance, soft touch feeling, ease of insertion into the human body. The injector injects ciproflaxin uniformly distributed in a hydrogel. The injector injects a drug in a hydrogel that is released at a predetermined timing. The injector injects a chemical material that reduces implant rejection, transplant rejection, foreign tissue rejection, or capsular contracture. The injector injects hyaluronic acid (HA) or polyvinyl alcohol (PVA) into a dermal area, a face area, a lip area, a breast area, or a buttock area. Computerized planning tools can be provided to enable doctors to plan specific injection sites to achieve desired cosmetic effects on the patients. The tools can guide the doctors or professionals to achieve the desired effects.

Other implementations may include one or more of the following. The system includes morphing or project the shape/size of breast or butt increase onto the 3D model of patient. A user can select from a library of wardrobes to provide realistic post-implant simulation. The system can inject a polymer into the shell of a soft tissue human implant prior to or during implantation of the shell with a lumen in a human body. The system can cross-link the polymer, wherein a cross linking reaction occurs outside the shell or in-situ inside the shell. The polymer can be one of: collagens, hyaluronic acids, celluloses, proteins, saccharides. The polymer can be an extracellular matrix of a biological system. Cross linkers can be used to from homo-polymers or to form copolymers by crosslinking with other polymer species. The filler material can control drug releases at predetermined timing in anticipation of an onset of a negative physiological event in response to invading foreign bodies. The system can inject anesthetics, lidocaine or compound to reduce or eliminate acute inflammatory reactions to the pharmaceutical substance. One or more compositions can be added and be selected from the group consisting of steroids, corticosteroids, dexamethasone, triamcinolone. The injector includes a medicament container, a needle, an energy source, and a regulator. The injector medicament container has a piston movably disposed therein such that the medicament container is divided into a first portion and a second portion. The first portion of the medicament container is configured to contain a filler, wherein the needle is coupled to the medicament container such that the needle is in fluid communication with the first portion of the medicament container. The methods include injecting a bolus of hyaluronic acid deep into the skin.

Other implementations of the above aspect can include one or more of the following. The system can be implanted through a cannula or needle, and can be filled with medicaments or chemical agents that would be useful in treating the patient including beneficial medications, chemical agents, hormonal treatments, stem cells, such as adipocytes, cellular precursors and components, and radiation media can be instilled to enhance the treatment capabilities of the implant in cancer and other breast or butt pathology.

Advantages of the preferred embodiments may include one or more of the following. The methods of the present invention are particularly beneficial for improving the contours of the breast or butts or buttocks, without requiring the use of surgical procedures. The system alleviates the difficulty of introducing breast or butt implants, and thus limiting greatly both the damage to implants and trauma to patient tissues. The system greatly reduces the need to manipulate the breast or butt implant in to place in the formed body cavity, and as a consequence greatly reduces postoperative infection. The hyaluronic acid enables soft tissue augmentation of the human body such as face, breast, buttocks and any soft tissue areas of the body. The injectable solution fills up the soft tissue are in question and is absorb by the body over the course of several months to a year. This injection alleviates the need for anesthesia and surgical placement of breast or butt or buttocks implants or autologus fat harvesting and injections. The entry wound is a small puncture and leaves no large permanent scars like the surgical approach. Since it is minimally invasive, the recovery time is much quicker and the down time from the procedure is almost eliminated completely. The system is ideal for the lean, athletic individual who doesn't have any fat to transfer and because of the high metabolic rate of the said individual it would burn the fat off anyway. The system would allow easy soft tissue augmentation in these types of patients. The easy non-surgical deployment of the system allows quick and easy soft tissue augmentation of the body whether it be for cosmetic such as breast or butt augmentation, buttocks augmentation, facial rejuvenation, and penile augmentation (enlargement), or reconstructive purposes where the is a soft tissue defect and lack of donor material. The soft tissue can easily be augmented precisely, quickly, with minimal recovery and scaring from a surgical incision by using the system any time that the needs arises without the need for fat harvesting, anesthesia, or surgery.

BRIEF DESCRIPTION OF THE DRAWINGS

FIGS. 2A-2B show exemplary processes that work with the system of FIG. 1.

FIGS. 7A-7E show exemplary hydrogel fabrication processes that can produce large volume of gels for minimally invasive body augmentation.

FIG. 8A shows exemplary HA-PVA bonding configurations with ester bonding, while

FIG. 11 shows an exemplary hydrogel fabrication process that can produce large volume of gels with anti-inflammatory drugs or agents.

DESCRIPTION

As a preface to the detailed description, it should be noted that, as used in this specification and the appended claims, the singular forms "a", "an", and "the" include plural referents, unless the context clearly dictates otherwise. All percentages (%) listed for gas constituents are % by volume, unless otherwise indicated.

The term "hyaluronic acid" (HA) as used in the present application refers to hyaluronic acid or salts of hyaluronic acid, such as the sodium, potassium, magnesium and calcium salts, among others. The term "hyaluronic acid" is also intended to include not only elemental hyaluronic acid, but hyaluronic acid with other trace of elements or in various compositions with other elements, as long as the chemical and physical properties of hyaluronic acid remain unchanged. In addition, the term "hyaluronic acid" as used in the present application is intended to include natural formulas, synthetic formulas or combination of these natural and synthetic formulas.

Figure 1:
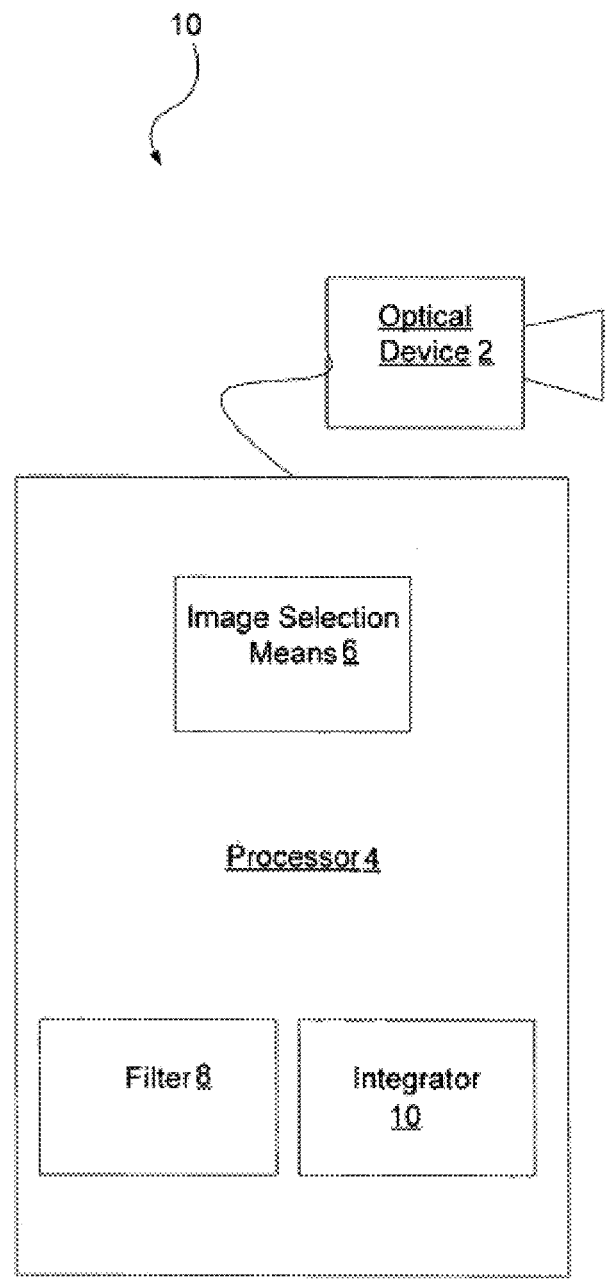
FIG. 1 shows an exemplary system to aid medical professionals such as doctors, plastic surgeons, and nurses to perform cosmetic enhancements on a patient.

FIG. 1 shows an exemplary system to aid medical professionals such as doctors, plastic surgeons, and nurses to perform cosmetic enhancements on a patient. In this system, the 3D imaging system (10) generally includes a camera or optical device (2) for capturing 3D images and a processor (4) that processes the 3D images to construct a 3D model. According to one exemplary embodiment illustrated in FIG. 1, the processor (4) includes means for selecting 3D images (6), a filter (8) that removes unreliable or undesirable areas from each selected 3D image, and an integrator (10) that integrates the 3D images to form a mosaic image that, when completed, forms a 3D model. The optical device (2) illustrated in FIG. 1 can be, according to one exemplary embodiment, a 3D camera configured to acquire full-frame 3D range images of objects in a scene, where the value of each pixel in an acquired 2D digital image accurately represents a distance from the optical device's focal point to a corresponding point on the object's surface. From this data, the (x,y,z) coordinates for all visible points on the object's surface for the 2D digital image can be calculated based on the optical device's geometric parameters including, but in no way limited to, geometric position and orientation of a camera with respect to a fixed world coordinate, camera focus length, lens radial distortion coefficients, and the like. The collective array of (x,y,z) data corresponding to pixel locations on the acquired 2D digital image will be referred to as a "3D image". Alternatively, the 3D camera can simply be two cameras spaced apart at a predetermined distance to provide 3D perspective capture. 3D image integration can be done using pre-calibrated camera positions to align multiple 3D images to merge the aligned 3D images into a complete 3D model. More specifically, cameras can be calibrated to determine the physical relative position of the camera to a world coordinate system. Using the calibration parameters, the 3D images captured by the camera are registered into the world coordinate system through homogeneous transformations. While traditionally effective, this method requires extensive information about the camera's position for each 3D image, severely limiting the flexibility in which the camera's position can be moved. The data capture can be viewed in an exemplary modeling system, according to one exemplary embodiment. The exemplary modeling system can support 3D image acquisition or capture, visualization, measuring, alignment and merging, morphing, editing, compression and texture overlay, all controlled using a database manager.

In one embodiment, the system photographs a patient's body in 3D before her breast or butt procedure, captures linear and volumetric measurements, and creates an exact three dimensional replica of her body on screen. The doctor examines this model with the patient during the consultation, and performs a virtual breast or butt augmentation, breast or butt lift, or breast or butt reconstruction on the 3D model to visualize the expected result in advance of an actual surgical procedure. The photo-realistic result can be viewed from all angles, and implant size adjusted to most closely meet the patient's needs. This allows women for the first time to select implant size, shape, and position based on the expected outcome on their own body.

In another embodiment, a 3D webcam is used with two cameras spaced roughly the same distance apart as human eyes, for the stereoscopic effect. 3D data acquisition and object reconstruction can be performed using stereo image pairs. Stereo photogrammetry or photogrammetry based on a block of overlapped images is the primary approach for 3D mapping and object reconstruction using 2D images. Close-range photogrammetry where cameras or digital cameras can be used to capture the close-look images of objects, e.g., breast or butts, and reconstruct them using the very same theory as the aerial photogrammetry.

Once the 3D model of the implant is finalized, the patient may wish to view the "try on" implants in combination with various articles of clothing to more fully determine how the implants will affect the patient's appearance. A library of wardrobe can be placed over the patient, so the patient can preview her implants with various items of clothing. Photorealistic images of the patient can be generated for the patient to consult family or friends as to which size implants gives the most favorable appearance. Thus, the system provides patients with the ability to realistically determine how a range of implant sizes will change their appearance.

A relatively large amount of hyaluronic acid, for example an entire syringe, is emptied into one area creating a large volume of the hyaluronic acid material in the deep tissue that does not break down readily. The deep volume or bolus can be sculpted by the doctor to enlarge or change the shape of the buttock or breast. The system injectable material comes in packages of 25, 50, 100, and 200 cc in volume. The delivery system is completely sterile and can be used in an outpatient setting or doctor's office. Since the volume of the system can be adjusted accordingly by the physician, the amount of soft tissue augmentation is limited only by the site. The system can also be additive just like MIBA Medical's Restor, Restylane or Allergan's Juvederm for augmenting facial wrinkles.

In yet another embodiment, an anti-inflammatory drug coating can be added to the hyaluronic acid injection. Exemplary drugs can include dexamethasone sodium acetate and other similar drugs used widely in pace makers and defibrillator leads system. An example list of drugs is as follows:

Anti-inflammatory (arthrotec, asacol, auralgan, azulfidine, bextra, celestone, daypro, deltasone, diclofenac, etodolac, indocin, ketoprofen, iodine, mobic, nabumetone, naproxen, piroxicam, ponstan, prednisone, rofecoxib, salofalk, solumedrol).

Antibiotics (Amlodipine, Besylate, Amoxicillin, Amoxil, Amphotericin, Ampicillin, Augmentin, Avelox, Bactrim, Bactroban, Biaxin, Ceftriaxone, Cefzil, Cephalexin, Chloramphenicol, Cipro XR, Clostebol, Cloxacillin, Cotrim, Daraprim, Dicloxacillin, Doxycycline, Eryacne, Erythromycin, Ethambutol)

Anti-aging compounds

Anti-oxidants

In another embodiment, a mixture of polyglycollic acid (PGA), and cross-linked hyaluronic acid (HA) can be used. These mixtures are combined in a foam/gel like injectable much similar to shaving cream/gel. This mixture also incorporates a broad spectrum antibiotic and corticosteroids to help prevent infection and reduce swelling. This way after introducing it into the subcutaneous soft tissue area to be augmented, it will fill up and be moldable and shapeable to the desired shape. The porous nature of the injectable allows the body to naturally fill up with the body natural fluids making it very natural in feel and look.

In one embodiment, one or more of these drugs may be incorporated into gel formulation to affect controlled delivery. The level of control over the delivery of the drug depends on the interaction between the specific drug and the polymer. The interactions are usually at the functional group level. The properties that affect the controls on the delivery are solubility, diffusion, and permeability between the polymer and the drug or drugs.

In yet another embodiment, a biocompatible polymer with a modulus that matches the modulus of the surrounding tissue may be used for natural feel and appearance. The polymer is a hydrogel that will absorb a preset amount of water will be used to control the specific desired modulus. To control the shape of the polymer, the outer surface maybe lightly cross-linked so that it will not flow into locations that are not desired. The cross-linking is gradient and light enough so that it will more elastomeric.

The system also provides improved methods of delivering sustained therapeutic dosages of medicines for extended periods. This would be more convenient to patients and reduce occurrences of missed doses. In one embodiment where the implant provides injectable medicines, the implant with drugs contained therein can maintain therapeutic levels for weeks or longer. Zero-order kinetics, wherein blood levels of drugs would remain constant throughout the delivery period. This delivery is useful in certain classes of medicines intended, for example, for antibiotic delivery, heart and blood pressure maintenance, pain control, and antidepressants.

The system allows a user to select an implant size using computer aided model using high definition web cameras (webcams) that are inexpensively manufactured and therefore made widely available. The system is easy to use such that persons with no special knowledge or training can use the 3D modeling of the body in the privacy of their home. And finally, the system provides patients with the ability to realistically determine how a range of implant sizes will change their appearance.

FIG. 2A shows an exemplary process executed by the hardware of FIG. 1. In this process, the system captures 3D model of patient (50). The process then isolates the patient's breast or butt region (52). Next, the process models shape and size of breast or butt increase due to implant (54) and morphs or projects the shape/size of breast or butt increase onto the 3D model of patient (56). The process allows the professional or the patient to iterative change implant shapes/sizes until the patient is satisfied with new shape (58). The process can also allow the user to select from a library of wardrobes to provide realistic simulation (60). When the patient selected his or her shape/size, then the system guides the professional to inject provides feedback to the professional to deliver body-sculpting material to the patient (62).

Figure 2B:
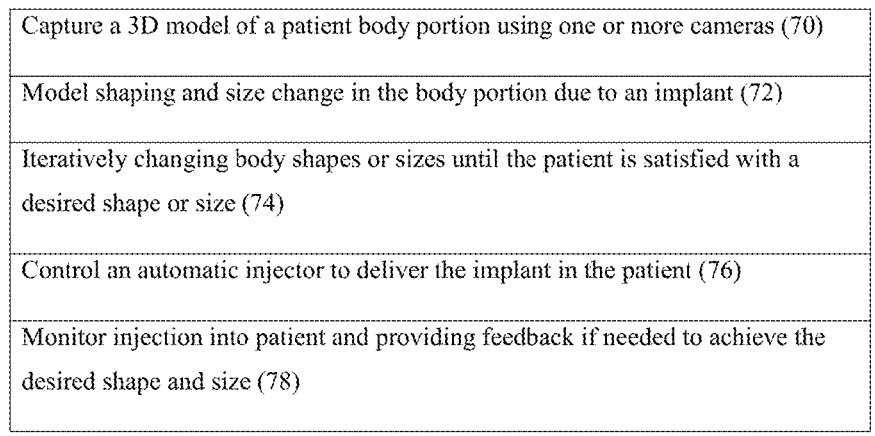

FIG. 2B shows another embodiment to augment human body portions. The process includes capturing a 3D model of a patient body portion using one or more cameras (70); modeling shape and size change in the body portion due to an implant (72); iteratively change body shapes or sizes until the patient is satisfied with a desired shape or size (74); controlling an automatic injector to deliver the implant in the patient (76); and monitoring injection into patient and providing feedback if needed to achieve the desired shape and size (78).

Figure 3:
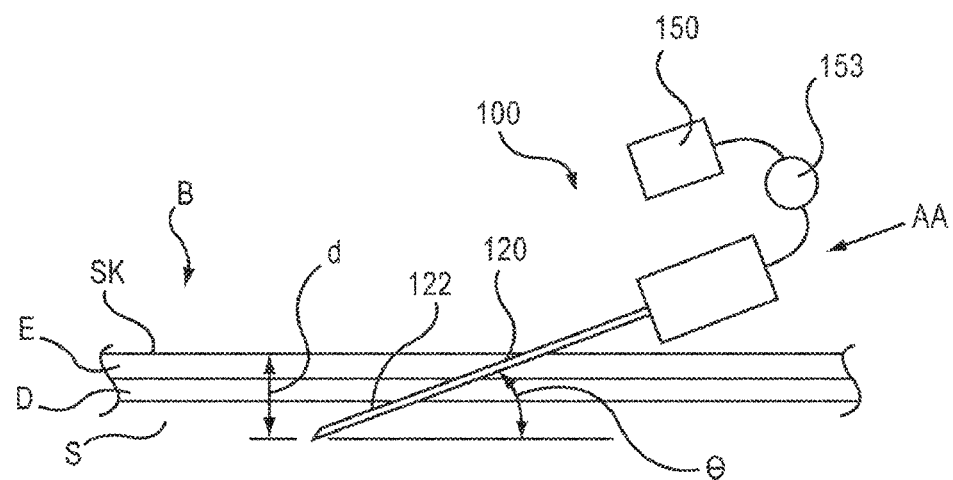
FIGS. 3-4 show exemplary filler injector devices.
Figure 4:
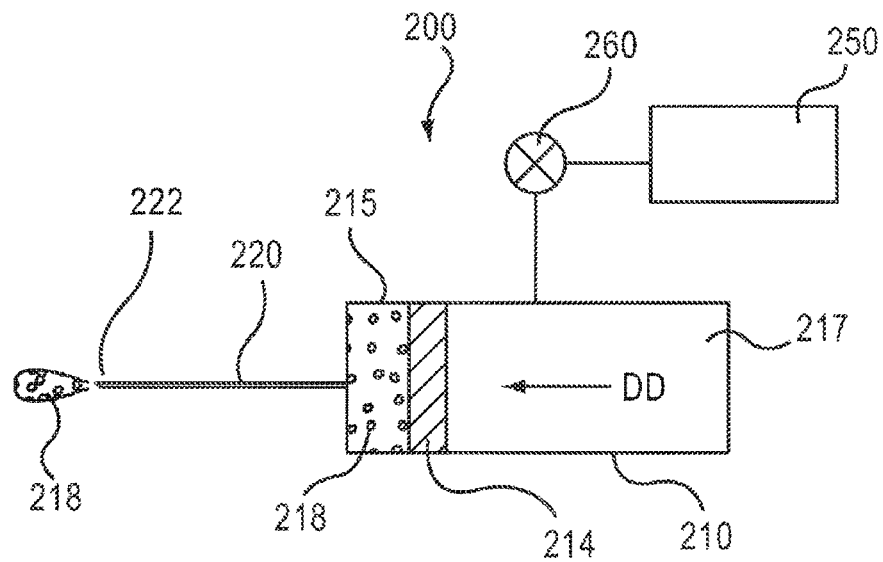

In one embodiment, the computer controls the automatic injector to fill the patient body portion to the correct shape and size. One exemplary injector is shown in FIGS. 3 and 4. FIG. 3 is a schematic illustration showing a portion of a body B containing a breast or butt filler 118 injected therein. The illustrated method includes inserting a distal end portion of a needle of a medical injector into a skin of a body. The skin can be disposed at any location of the body, such as for example, facial skin. Referring to FIG. 3, the distal end portion 122 of the needle 120 is inserted into the skin SK in a distal direction as shown by the arrow AA. The needle 120 is inserted into the skin SK at an angle Θ relative to the surface of the skin SK and at depth d within the body B. The needle 120 can be inserted into the skin SK at any suitable angle Θ and at any suitable depth d for achieving the desired result. In some embodiments, for example, the needle 120 is inserted into the skin SK at an angle Θ of between 5 and 35 degrees. In other embodiments, the needle 120 is inserted into the skin SK at an angle Θ of approximately 20 degrees. In some embodiments, for example, the needle 120 is inserted into the skin SK at a depth d of between 1.5 and 6 millimeters. In other embodiments, the needle 120 is inserted into the skin SK at a depth d of between approximately 1.5 and 2 millimeters. Although the distal end portion 122 of the needle 120 is shown as being inserted into the subcutaneous tissue S of the skin SK, in some embodiments, the distal end portion 122 of the needle 120 can be inserted into the epidermis E and/or the dermis D of the skin SK. In other embodiments, the distal end portion 122 of the needle 120 can be inserted below the subcutaneous tissue S. In yet other embodiments, the distal end portion 122 of the needle 120 can be inserted through the skin SK into another portion of the body B, such as for example a urinary sphincter. An energy source operatively coupled to the medical injector is actuated such that a breast or butt filler is conveyed from the medical injector into the skin through the distal end portion of the needle. The energy source 150 is actuated via an actuator 153. The energy source 150 can include any suitable form of energy that can act upon the medical injector 100 to convey the breast or butt filler 118 from the medical injector 100 through the distal end portion 122 of the needle 120. For example, in some embodiments, the energy source 150 can include a pressurized gas that exerts a force on a portion of the medical injector 100. When the energy source 150 is actuated by the actuator 153, the breast or butt filler 118 is conveyed from the medical injector 100 through the distal end portion 122 of the needle 120. In this manner, the breast or butt filler 118 can be injected into the body B non-manually. Said another way, the breast or butt filler 118 can be injected into the body B without the user producing the energy necessary for the injection.

The distal end portion of the needle is moved within the skin when the energy source is being actuated. In this manner, the user can vary the location of the distal end portion of the needle within the skin when the breast or butt filler is being injected into the body B. The distal end portion 122 of the needle 120 can moved in a proximal direction, when the energy source 150 is being actuated. In this manner, the user can inject a substantially continuous bead of breast or butt filler 118 along a desired passageway (e.g., a breast or butt implant) within the skin SK. More particularly, the distal end portion 122 of the needle 120 is moved in a direction substantially opposite the direction of flow of the breast or butt filler 118 from the distal end portion 122 of the needle 120.

Because the body sculpting filler 118 is conveyed from the distal end portion 122 of the needle 120 non-manually, the user is not burdened with producing a force in the distal direction (to inject the filler 118) while simultaneously moving the distal end portion 122 of the needle 120 in the proximal direction. In this manner, the operation of producing a force to inject the filler 118 is independent from the operation of moving the distal end portion 122 of the needle 120. Similarly stated, the operation of producing a force to inject the filler 118 is decoupled from (i.e., is separate and distinct from) the operation of moving the distal end portion 122 of the needle 120. This arrangement can result in a repeatable, continuous and/or controlled movement of the distal end portion 122 of the needle 120 and/or injection of the filler 118. In contrast, some known medical injectors require the user to use the same hand to produce a force in a distal direction along a longitudinal axis of the medical injector to inject a breast or butt filler and move the needle along the longitudinal axis, for example, in an opposite (i.e., proximal) direction. In such instances, the injection of the breast or butt filler can be irregular, uncontrolled and/or discontinuous. For example, when injecting high viscosity breast or butt fillers using known medical injectors, it can be difficult for the user to maintain the force necessary to inject the breast or butt filler at the desired flow rate throughout the injection event. Thus, when injecting high viscosity fillers using known medical injectors, the resulting bead of breast or butt filler can have undesirable spatial variability in its size and/or volume.

Although the distal end portion 122 of the needle 120 is shown and described above as being moved in the proximal direction when the energy source 150 is being actuated, in other embodiments, the distal end portion 122 can be moved in any manner. For example, in some embodiments the distal end portion 122 of the needle 120 can be moved in a distal direction (i.e., in substantially the same direction as the flow of the breast or butt filler 118 from the distal end portion 122 of the needle 120). In other embodiments, the distal end portion 122 of the needle 120 can be moved in a direction not parallel to a longitudinal axis of the needle 120. In yet other embodiments, the distal end portion 122 of the needle 120 can be rotated when the energy source 150 is being actuated. For example, in some embodiments, the user can "fan" the distal end portion 122 of the needle 120 (i.e., move the distal end portion 122 in a direction not parallel to a longitudinal axis of the needle 120) within the skin SK when the energy source is being actuated. Moreover, the distal end portion 122 of the needle 120 can be moved any suitable distance when the energy source 150 is being actuated. In some embodiments, for example, the distal end portion 122 of the needle 120 can be moved a distance of at least 4 millimeters during actuation of the energy source 150.

Returning to the flow chart shown in FIG. 1, in some embodiments, the method can optionally include regulating a flow rate of the breast or butt filler through the distal end portion of the needle when the energy source is being actuated, at 18. In this manner, the user can adjust the amount the breast or butt filler being injected within and/or beneath the skin to provide the desired cosmetic and/or therapeutic results. In some embodiments, for example, the flow rate of the breast or butt filler can be regulated to maintain a substantially constant flow rate of the breast or butt filler through the distal end portion of the needle when the distal end portion of the needle is moved within and/or beneath the skin. Said another way, in some embodiments, the flow rate of the breast or butt filler can be regulated to produce a substantially uniform bead of breast or butt filler within the skin. In some embodiments, for example, the flow rate of the breast or butt filler can be regulated when the needle is moved within the skin to produce a substantially uniform bead of breast or butt filler having a volume of approximately 1 to 2 cubic centimeters and a length of between approximately 4 millimeters and 13 millimeters. In other embodiments, the flow rate of the breast or butt filler can be regulated when the needle is moved within the skin to produce a substantially uniform bead of breast or butt filler having a volume of less than 1 cubic centimeter and a length of between approximately 4 millimeters and 13 millimeters. For example, in some embodiments, the flow rate of the breast or butt filler can be regulated when the needle is moved within the skin to produce a substantially uniform bead of breast or butt filler having a volume of approximately 0.1 to 0.2 cubic centimeter and a length of between approximately 4 millimeters and 13 millimeters. In yet other embodiments, the flow rate of the breast or butt filler can be regulated when the needle is moved within the skin to produce a substantially uniform bead of breast or butt filler having a volume of greater than 2 cubic centimeter (e.g., a volume of 3, 4, 5, or 10 cubic centimeters) and a length of up to 150 millimeters. Such a bead can be used, for example, to increase the skin volume in the areas of the nasal labial fold, the jowls and/or the neck region, and can smooth the appearance of wrinkles in those areas. The flow rate of the breast or butt filler can be regulated to produce any suitable flow rate. For example, in some embodiments, the flow rate of the breast or butt filler can be regulated to a substantially constant flow rate of at least approximately 0.02 cubic centimeters per minute. In other embodiments, the flow rate of the breast or butt filler can be regulated to a substantially constant flow rate of between approximately 0.02 cubic centimeters per minute and 0.5 cubic centimeters per minute. In yet other embodiments, the flow rate of the breast or butt filler can be regulated to a substantially constant flow rate of as much as 3 cubic centimeters per minute. In still other embodiments, the flow rate of the breast or butt filler can be regulated to a substantially constant flow rate greater than 3 cubic centimeters per minute. Although the flow rate of the breast or butt filler through the distal end portion of the needle is described above as being regulated to a substantially constant value when the needle is moved within the body, in some embodiments, the flow rate of the breast or butt filler can be selectively varied during the injection process. In this manner, the user can produce a bead and/or set of beads of breast or butt filler within the skin having spatially varied volume. Moreover, in some embodiments, the method 10 can include optionally regulating a flow rate of the breast or butt filler through the distal end portion of the needle such that the flow rate is substantially zero at a first time after the needle has been moved and still remains in the skin. In some embodiments, the system can include optionally stopping the flow of the breast or butt filler through the distal end portion of the needle after the needle has been moved within the skin. The distal end portion of the needle can then be moved while the flow rate of the breast or butt filler through the distal end portion of the needle is zero. The flow rate of the breast or butt filler through the distal end portion of the needle can then be regulated such that the flow rate is increased greater than zero. In this manner, the user can produce a discontinuous bead and/or set of beads of filler within the skin. In some embodiments, for example, the flow rate of the breast or butt filler through the distal end portion of the needle can be regulated such that at least one discrete bead from the set of beads has a volume of approximately 0.1 cubic centimeters or less. In other embodiments, the flow rate of the breast or butt filler through the distal end portion of the needle can be regulated such that at least one discrete bead from the set of beads has a volume of less than approximately 0.01 cubic centimeters or less. In some embodiments, the flow rate of the breast or butt filler through the distal end portion of the needle can be regulated to produce such a set of discontinuous beads in areas of the skin surrounding the eye.

The flow rate of the breast or butt filler through the distal end portion of the needle can be regulated in any suitable manner. For example, the flow rate of the breast or butt filler 118 through the distal end portion 122 of the needle 120 can be regulated by selectively controlling the energy from the energy source 150 to the medical injector 100. Said another way, in some embodiments, the flow rate of the breast or butt filler 118 through the distal end portion 122 of the needle 120 can be regulated by mechanisms outside of the flow path of the breast or butt filler 118. Moreover, in some embodiments, the flow rate of the breast or butt filler 118 through the distal end portion 122 of the needle 120 can be regulated via the actuator 153. For example, in some embodiments, the user can repeatedly and/or controllably actuate the energy source 150 using the actuator 153. Said another way, in some embodiments, the user can repeatedly toggle the actuator 153 to selectively couple the energy source 150 to and decouple the energy source 150 from the medicament injector 100. In this manner, for example, the flow rate of the breast or butt filler can be regulated to produce a discontinuous bead and/or set of beads of breast or butt filler within the skin, as described above. In other embodiments, the flow rate of the breast or butt filler 118 through the distal end portion 122 of the needle 120 can be regulated by selectively restricting the flow path of the breast or butt filler 118 within the medical injector 100 and/or the needle 120. For example, in some embodiments, the flow rate of the breast or butt filler 118 through the distal end portion 122 of the needle 120 can be regulated by a valve within the medicament flow path.

FIG. 4 illustrates a medical device 200, according to an embodiment configured inject a medicament 218. The medical device 200 includes a medicament container 210, a needle 220, an energy source 250 and a regulator 260. The medicament container 210 includes a piston 214 movably disposed therein, such that the medicament container 210 is divided into a first portion 215 and a second portion 217. In some embodiments, for example, the piston 214 can be disposed within the medicament container 210 such that the first portion 215 of the medicament container 210 is fluidically isolated from the second portion 217 of the medicament container 217.

The first portion 215 of the medicament container 210 is configured to contain a medicament 218 having a high viscosity (i.e., a medicament having a viscosity of at least 100 Poise). The medicament 218 can be any medicament suitable for being injected into a body. For example, in some embodiments, the medicament 218 can be a high viscosity dermal filler (e.g., a liquid dermal filler, a paste-like dermal filler, a dermal filler including both a liquid component and a solid component, or the like). In some embodiments, the medicament 218 can have a viscosity of at least 1000 Poise (100 N-sec/m2). In other embodiments, the medicament 218 can have a viscosity of at least 10,000 Poise. In yet other embodiments, the medicament 218 can have a viscosity of at least 100,000 Poise.

In some embodiments, the medicament 218 can be a fluid that is characterized by a substantially linear shear stress as a function of the rate of shear strain applied thereto. Said another way, in some embodiments, the medicament 218 can be a Newtonian fluid having a viscosity that varies substantially only as a function of its temperature and pressure. In other embodiments, the medicament 218 can be a fluid that is characterized by a non-linear shear stress as a function of the rate of shear strain applied thereto. Said another way, in some embodiments, the medicament 218 can be a non-Newtonian fluid having a viscosity that varies according other factors, such as, for example, the magnitude of and/or rate of increase of a force applied to the medicament 218.

The needle 220 is coupled to the medicament container 210 such that the needle 220 is in fluid communication with the first portion 215 of the medicament container 210. The needle 220 can be coupled to the medicament container 210 by any suitable mechanism. For example, in some embodiments, the needle 220 can be coupled to the medicament container 210 by a Luer fitting that provides a substantially fluid-tight seal (i.e., a seal that that substantially prevents a liquid and/or a gas from passing therethrough) between the needle 220 and the medicament container 210. In some embodiments, the fluid-tight seal can be a hermetic seal (i.e., a seal that substantially prevents a gas from passing therethrough).

The needle 220 can have any suitable bore size and length. For example, in some embodiments, the needle can have a small bore to reduce patient discomfort during a procedure. For example, in some embodiments, the needle 220 can define a lumen having a nominal inner diameter of less than or equal to approximately 0.191 millimeters (i.e., a 27 gauge needle). In other embodiments, the needle 220 can define a lumen having a nominal inner diameter of less than or equal to approximately 0.140 millimeters (i.e., a 30 gauge needle). In some embodiments, for example, the needle 220 can define a lumen having a nominal inner diameter of approximately 0.114 millimeters (i.e., a 31 gauge needle). In some embodiments, for example, the needle 220 can define a lumen having a nominal inner diameter of approximately 0.089 millimeters (i.e., a 32 gauge needle). In some embodiments, the needle 220 can have a length of at least 17 millimeters.

When the piston 214 moves within the medicament container 210, as shown by the arrow DD in FIG. 4, the medicament 218 is conveyed from the first portion 215 of the medicament container 210. Said another way, a user can inject the medicament 218 into a body by actuating the medical device 200 to cause the piston 214 to move distally within the medicament container 210. The energy source 250 is operatively coupled to the piston 214 such that the piston 214 can be moved non-manually. The energy source 250 can be any suitable form of energy configured produce kinetic energy to move the piston 214 within the medicament container 210. The amount of kinetic energy required to move the piston 214 within the medicament container 210 is dependent on, among other things, the viscosity of the medicament 218, the desired flow rate of the medicament 218 through the distal end portion 222 of the needle 220, the length of the needle 220 and/or the size of the lumen defined by the needle 220. In some embodiments, the energy source 250 can produce kinetic energy sufficient to move the piston 214 such that a medicament 218 having a viscosity of at least 1000 Poise can be injected through the distal end portion 222 of the needle at a flow rate of at least 0.02 cubic centimeters per minute. In other embodiments, the energy source 250 can produce kinetic energy sufficient to move the piston 214 such that a medicament 218 having a viscosity of at least 1000 Poise can be injected through the distal end portion 222 of the needle at a flow rate of at least 0.5 cubic centimeters per minute. In yet other embodiments, the energy source 250 can produce kinetic energy sufficient to move the piston 214 such that a medicament 218 having a viscosity of at least 10,000 Poise can be injected through the distal end portion 222 of the needle 220 at a flow rate of at least 0.5 cubic centimeters per minute. In still other embodiments, the energy source 250 can produce kinetic energy sufficient to move the piston 214 such that a medicament 218 having a viscosity of at least 10,000 Poise can be injected through the distal end portion 222 of the needle 220 at a flow rate of at least 3 cubic centimeters per minute. In still other embodiments, the energy source 250 can produce kinetic energy sufficient to move the piston 214 such that a medicament 218 having a viscosity of at least 10,000 Poise can be injected through the distal end portion 222 of the needle 220 at a flow rate of between 3 and 5 cubic centimeters per minute.

Additionally, the pressure of the medicament 218 within the medicament container 210 during an injection event is related to the kinetic energy applied to the piston 214, and is therefore also dependent on, among other things, the viscosity of the medicament 218, the desired flow rate of the medicament 218 through the distal end portion 222 of the needle 220, the length of the needle 220 and/or the size of the lumen defined by the needle 220. In certain circumstances, the pressure of the medicament 218 within the medicament container 210 can be modeled by the Hagen-Poiseuille law, as indicated below:

$$P = (8 * \mu * L * Q)/(\Pi * R4) \qquad (1)$$

where P is the pressure of the medicament 218 within the medicament container, μ is the viscosity of the medicament 218, L is the length of the needle 220, Q is the flow rate of the medicament 218 through the distal end portion 222 of the needle 220, and R is the radius of the lumen defined by the needle 220. Because the pressure required to inject a high viscosity fluid through a small-bore needle is proportional to the inverse of the radius of the lumen of the needle to the fourth power, the pressure of the medicament 218 within the medicament container 210 necessary to achieve the desired flow rate can, at times, be relatively high. In some embodiments, the energy source 250 can be configured to move the piston 214 within the medicament container 210 such that a pressure of the medicament 218 within the medicament container 210 is greater than 345 kilopascals (50 p.s.i.). In other embodiments, the energy source 250 can be configured to move the piston 214 within the medicament container 210 such that a pressure of the medicament 218 within the medicament container 210 is greater than 690 kilopascals (100 p.s.i.). In still other embodiments, the energy source 250 can be configured to move the piston 214 within the medicament container 210 such that a pressure of the medicament 218 within the medicament container 210 is greater than 1035 kilopascals (150 p.s.i.). In still other embodiments, the energy source 250 can be configured to move the piston 214 within the medicament container 210 such that a pressure of the medicament 218 within the medicament container 210 is greater than 34.5 Megapascals (5000 p.s.i.).

The regulator 260 is configured to regulate the flow rate of the medicament 218 through the distal end portion 222 of the needle 220. In this manner, the user can adjust the flow rate of the medicament 218 through the distal end portion 222 of the needle 220. In some embodiments, for example, the regulator 260 can substantially stop the flow of the medicament 218 through the distal end portion 222 of the needle 220. In this manner, as described above, the user can discontinuously inject the medicament 218 within the body.

The regulator 260 can be any suitable mechanism for regulating the flow rate of the medicament 218 through the distal end portion 222 of the needle 220. As described above, in some embodiments, the regulator 260 can control the transmission of energy from the energy source 250 to the piston 214. In other embodiments, the regulator 260 can selectively restrict the flow path of the medicament 218 within the first portion 215 of the medicament container 210 and/or the needle 220. The above system can provide soft tissue augmentation including breast implant, butt implant, facial rejuvenation, penile enhancement, and body reconstruction. The system allows for breast or butt enlargements to be made with fine attenuation. The system provides a naturally smooth skin without requiring complex surgery. The desired effect can be achieved quickly and with minimally invasive surgery. The risk of infection can be reduced due to the minimally invasive therapy. The gel material that filled the balloon is compliant at different frequencies with the surrounding tissue so that it matches the response of the tissue to the exterior touches, thus creating the natural feelings to touches at the site. The compliant nature of the gel filler makes the expression of the patient to appear more natural than other procedures by not distorting the natural the breast or butt contours. The filler material, being a higher molecular gel, allows an implant material such as halyuronic acid to be used which allows continuous zero order drug delivery method, the most desirable controlled delivery method.

The methods of the invention involve administering injections into the deep part of the skin (i.e., deep fat or just above the bone) using large injections of a hyaluronic acid composition that has been formulated for injection into the superficial part of the skin covering the breast or butt or buttock. One of skill in the art will appreciate that the depth at with the injection is made will vary depending on the specific injection site. Further, the injections can be administered without requiring large bore needles or surgical incisions, as the methods of the present invention utilize small bore needles. Preferably, the hyaluronic acid bolus is injected into the skin using a needle having a gauge of from 24 (0.559 mm) to 30 (0.305 mm), where the bolus is more preferably injected using a needle having a gauge of from 26 (0.457 mm) to 28 (0.356 mm), and is most preferably injected using a 27 gauge needle (0.406 mm). In other embodiments of this invention, the hyaluronic acid bolus can be injected using a small canullae from 1-2 mm in diameter to deliver larger bolus with higher viscosity.

In some embodiments of this invention, about 1.5 to 6, preferably about 3 to 4, full syringes (for example 0.7 cc or 0.8 cc syringes) can be injected on each side of the subject's facial rhytids to eleviate the wrinkles. It is preferred that at least 1 cc, more preferably at least 2 cc, even more preferably about 2 to 3 cc, are injected on each side. One of skill in the art will appreciate that the amount of hyaluronic acid to be injected will also vary depending on the specific injection site.

In other embodiments of this invention, about 50 to 400 cc, can be injected on each side of the subject's breast or buttocks to enhance its curvature. Again, one of skill in the art will appreciate that the amount of hyaluronic acid to be injected will also vary depending on the specific injection site.

In some embodiments, for example, an apparatus includes a 3D imaging system coupled to a computer that controls medical injector, a medicament container, a needle, an energy source, and a regulator. The medicament container has a piston movably disposed therein such that the medicament container is divided into a first portion and a second portion. The first portion of the medicament container is configured to contain a medicament, such as, for example a dermal filler. The needle is coupled to the medicament container such that the needle is in fluid communication with the first portion of the medicament container. The energy source is operatively coupled to the piston and is configured to produce a kinetic energy to move the piston within the medicament container such that the medicament having a viscosity of at least 1000 Poise (100 N-sec/m2) can be conveyed from the first portion of the medicament container through a distal end of the needle at a flow rate of at least 0.02 cubic centimeters per minute. The regulator is configured to regulate the flow rate of the medicament through the distal end of the needle.

In some embodiments, for example, an apparatus includes a 3D imaging system coupled to a computer that controls medical injector, a pressurized fluid source, and a regulator. The medical injector is configured to contain halyuronic acid filler, and includes a needle. The needle defines a lumen therethrough having a nominal inner diameter of less than approximately 0.140 millimeters (i.e., the needle is smaller than 30 gauge), and has a length of at least 17 millimeters. The pressurized fluid source, which can include, for example, a canister of pressurized fluid, is operatively coupled to the medical injector. A pressurized fluid from the pressurized fluid source has a pressure of at least 345 kilopascals. The pressurized fluid is configured to actuate the medical injector such that the dermal filler can be conveyed from the medical injector through the lumen of the needle. The regulator is configured to regulate the flow rate of the dermal filler through the lumen of the needle.

The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein.

Rooster combs are a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP0694616 discloses fermentation processes using an improved strain of *Streptococcus zooepidemicus* with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive *Bacillus* host.

Hyaluronan synthases have been described from vertebrates, bacterial pathogens, and algal viruses (DeAngelis, P. L., 1999, Cell. Mol. Life Sci. 56: 670-682). WO 99/23227 discloses a Group I hyaluronate synthase from *Streptococcus equisimilis*. WO 99/51265 and WO 00/27437 describe a Group II hyaluronate synthase from *Pasteurella multocida*. Ferretti et al. discloses the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (Proc. Natl. Acad. Sci. USA. 98, 4658-4663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as lyophilization or spraydrying.

The term "microbead" is used herein interchangeably with microdrop, microdroplet, microparticle, microsphere, nanobead, nanodrop, nanodroplet, nanoparticle, nanosphere etc. A typical microbead is approximately spherical and has an number average cross-section or diameter in the range of between 1 nanometer to 1 millimeter. Though, usually the microbeads of the one embodiment will be made with a desired size in a much more narrow range, i.e., they will be fairly uniform. The microbeads preferably have a diameter in the range of about 100-1,000 nanometer; or in the range of 1,000 nanometer to 1,000 micrometer. The size-distribution of the microbeads will be low and the polydispersibility narrow.

Host Cells

A preferred embodiment relates to the method of the first aspect, wherein the hyaluronic acid or salt thereof is recombinantly produced, preferably by a Gram-positive bacterium or host cell, more preferably by a bacterium of the genus *Bacillus*.

The host cell may be any *Bacillus* cell suitable for recombinant production of hyaluronic acid. The *Bacillus* host cell may be a wild-type *Bacillus* cell or a mutant thereof *Bacillus* cells useful in the practice of the one embodiment include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. Mutant *Bacillus subtilis* cells particularly adapted for recombinant expression are described in WO 98/22598. Non-encapsulating *Bacillus* cells are particularly useful in the one embodiment.

In one embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus clausii* cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164Δ5 (see U.S. Pat. No. 5,891,701) or *Bacillus subtilis* 168Δ4.

Molecular Weight

The content of hyaluronic acid may be determined according to the modified carbazole method (Bitter and Muir, 1962, Anal Biochem. 4: 330-334). Moreover, the number average molecular weight of the hyaluronic acid may be determined using standard methods in the art, such as those described by Ueno et al., 1988, Chem. Pharm. Bull. 36, 4971-4975; Wyatt, 1993, Anal. Chim. Acta 272: 1-40; and Wyatt Technologies, 1999, "Light Scattering University DAWN Course Manual" and "DAWN EOS Manual" Wyatt Technology Corporation, Santa Barbara, Calif.

In one embodiment, the hyaluronic acid, or salt thereof, of the one embodiment has a molecular weight of about 10,000 to about 10,000,000 Da. In a more preferred embodiment it has a molecular weight of about 25,000 to about 5,000,000 Da. In a most preferred embodiment, the hyaluronic acid has a molecular weight of about 50,000 to about 3,000,000 Da.

In another embodiment, the hyaluronic acid or salt thereof has a molecular weight in the range of between 300,000 and 3,000,000; preferably in the range of between 400,000 and 2,500,000; more preferably in the range of between 500,000 and 2,000,000; and most preferably in the range of between 600,000 and 1,800,000.

In yet another embodiment, the hyaluronic acid or salt thereof has a low number average molecular weight in the range of between 10,000 and 800,000 Da; preferably in the range of between 20,000 and 600,000 Da; more preferably in the range of between 30,000 and 500,000 Da; even more preferably in the range of between 40,000 and 400,000 Da; and most preferably in the range of between 50,000 and 300,000 Da.

Salts and Crosslinked HA

One embodiment relates to a method of the first aspect, which comprises an inorganic salt of hyaluronic acid, preferably sodium hyaluronate, potassium hyaluronate, ammonium hyaluronate, calcium hyaluronate, magnesium hyaluronate, zinc hyaluronate, or cobalt hyaluronate.

Other Ingredients

In another embodiment, the product produced by the method of one embodiment may also comprise other ingredients, preferably one or more active ingredient, preferably one or more pharmacologically active substance, and also preferably a water-soluble excipient, such as lactose or a non-biologically derived sugar.

Non-limiting examples of an active ingredient or the one or more pharmacologically active substance(s) which may be used in the one embodiment include vitamin(s), anti-inflammatory drugs, antibiotics, bacteriostatics, general anaesthetic drugs, such as, lidocaine, morphine etc. as well as protein and/or peptide drugs, such as, human growth hormone, bovine growth hormone, porcine growth hormone, growth hormone releasing hormone/peptide, granulocyte-colony stimulating factor, granulocyte macrophage-colony stimulating factor, macrophage-colony stimulating factor, erythropoietin, bone morphogenic protein, interferon or derivative thereof, insulin or derivative thereof, atriopeptin-Ill, monoclonal antibody, tumor necrosis factor, macrophage activating factor, interleukin, tumor degenerating factor, insulin-like growth factor, epidermal growth factor, tissue plasminogen activator, factor IIV, factor HIV, and urokinase.

A water-soluble excipient may be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Several aspects of one embodiment relate to various compositions and pharmaceuticals comprising, among other constituents, an effective amount of the crosslinked HA product, and an active ingredient, preferably the active ingredient is a pharmacologically active agent; a pharmaceutically acceptable carrier, excipient or diluent, preferably a water-soluble excipient, and most preferably lactose.

In addition, aspects of one embodiment relate to articles comprising a product as defined in the first aspect or a composition as defined in the aspects and embodiments above, e.g., a sanitary article, a medical or surgical article. In a final aspect one embodiment relates to a medicament capsule or microcapsule comprising a product as defined in the first aspect or a composition as defined in other aspects and embodiments of one embodiment.

One method of producing crosslinked hyaluronic acid microbeads include:

(a) mixing an aqueous alkaline solution comprising hyaluronic acid, or a salt thereof, with a solution comprising a crosslinking agent;

(b) forming microdroplets having a desired size from the mixed solution of step (a) in an organic or oil phase to form a water in organic or water in oil (W/O) emulsion;

(c) continuously stirring the W/O emulsion, whereby the reaction of hyaluronic acid with divinylsulfone takes place to provide crosslinked hyaluronic acid microbeads; and (d) purifying the crosslinked hyaluronic acid microbeads.

It has previously been described how to produce hyaluronic acid recombinantly in a *Bacillus* host cell, see WO 2003/054163, Novozymes NS, which is incorporated herein in its entirety. The hyaluronic acid, or salt thereof, can also be recombinantly produced in a *Bacillus* host cell.

Various molecular weight fractions of hyaluronic acid have been described as advantageous for specific purposes.

One embodiment relates to a method of the first aspect, wherein the hyaluronic acid, or salt thereof, has an number average molecular weight of between 100 and 3,000 kDa, preferably between 500 and 2,000 kDa, and most preferably between 700 and 1,800 kDa. The initial concentration of hyaluronic acid, or a salt thereof, in the method of one embodiment, influences the properties of the resulting crosslinked microbeads. Therefore, one embodiment relates to a method of the first aspect, wherein the alkaline solution comprises dissolved hyaluronic acid, or salt thereof, in a concentration of between 0.1%-40% (w/v).

The pH value during the crosslinking reaction also influences the outcome, so in a preferred embodiment one embodiment relates to a method of the first aspect, wherein the alkaline solution comprises dissolved sodium hydroxide in a concentration of between 0.001-2.0 M. The concentration of the crosslinking agent has a profound impact on the resulting microbeads.

Consequently, one embodiment relates to a method of the first aspect, wherein the crosslinking agent is divinylsulfone (DVS); preferably DVS is comprised in the mixed solution of step (a) in a weight ratio of between 1:1 and 100:1 of HA/DVS (dry weight), preferably between 2:1 and 50:1 of HA/DVS (dry weight).

Other crosslinking agents are also envisioned as being suitable for the methods of the one embodiment, such as, crosslinking agents based on bisepoxide crosslinking technology: GDE=glycerol diglycidyl ether and BDE: 1,4-butanediol diglycidyl ether.

Crosslinking agents suitable for the methods of the one embodiment are for example poly functional (>=2) OH-reactive compounds. Examples for suitable crosslinking agents are divinylsulfone (DVS) or crosslinking agents based on bisepoxide crosslinking technology, for example GDE=glycerol diglycidyl ether or BDE: 1,4-butanediol diglycidyl ether. The crosslinking agent is preferably selected from divinylsulfone, glycerol diglycidyl ether or 1,4-butanediol diglycidyl ether. The most preferred crosslinking agent of one embodiment is divinylsulfone which is preferably used in the weight ratio mentioned above.

An initial period of stirring during and/or immediately after mixing the solution comprising the crosslinking agent and the HA-solution was desirable to achieve satisfactory gelling. Accordingly, one embodiment relates to a method of the first aspect, wherein the reaction of hyaluronic acid with divinylsulfone takes place at a temperature in the range of 5° C.-100° C., preferably in the range of 15° C.-50° C., more preferably in the range of 20° C.-30° C.

In another preferred embodiment, the stirring in step (c) is continued for a period of between 1-180 minutes.

A heating step can be beneficial after mixing the solutions. Accordingly, the mixed solution is heated to a temperature in the range of 20° C.-100° C., preferably in the range of 25° C.-80° C., more preferably in the range of 30° C.-60° C., and most preferably in the range of 35° C.-55° C., and the temperature is maintained in this range for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes after mixing the solutions; preferably without stirring.

It is advantageous to leave the reaction mixture at room temperature for a brief period after the crosslinking reaction has taken place, but still with continuous stirring.

In one embodiment, the reaction mixture is maintained after the reaction has taken place for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes, at a temperature in the range of 0° C.-40° C., preferably in the range of 10° C.-30° C. It might by advantageous when the microdroplets of step (b) have a number average diameter in the range of from about 1 nanometer to 1 millimeter. The maximum of the particle size distribution of the microdroplets of step (b) is preferably in the range of from 0.1 to 100 pm, more preferably from 0.5 to 10 μm and most preferably from 1 to 2 μm. The size of the droplets can be adjusted by the choice of emulsifier used and the intensity of stirring. The combination of emulsifier used and intensity of stirring necessary to obtain droplets with the desired size can be determined by simple test series. The microdroplets can have a number average diameter in the range of about 1 nanometer to 1 millimeter. It is also preferred that the crosslinked microbead of the second aspect has a number average diameter in the range of about 1 nanometer to 1 millimeter. It might be advantageous to obtain a dispersion in step (c) that comprises almost none unreacted crosslinking agent. Preferably the dispersion more preferably the microbeads comprise less than 10 ppm by weight (wppm), more preferably less than 5 wppm. The concentration of free crosslinking agent in the dispersion especially needs to be low if the dispersion is directly used in pharmaceutical or biomedical application/device compositions because the unreacted crosslinking agent might be a toxicological threat. It is therefore preferred to last the reaction of step (c) till a dispersion is obtained comprising the unreacted crosslinking agent in the concentration mentioned above.

Compounds from at least one of the following groups can be employed as nonionic emulsifiers or surfactants: addition products of from 2 to 100 mol of ethylene oxide and/or 0 to 5 mol of propylene oxide on linear fatty alcohols having 8 to 22 C atoms, on fatty acids having 12 to 22 C atoms and on alkylphenols having 8 to 15 C atoms in the alkyl group, C12/18-fatty acid mono- and diesters of addition products of from 1 to 100 mol of ethylene oxide on glycerol, glycerol mono- and diesters and sorbitan mono- and diesters of saturated and unsaturated fatty acids having 6 to 22 carbon atoms and ethylene oxide addition products thereof, alkyl mono- and oligoglycosides having 8 to 22 carbon atoms in the alkyl radical and ethylene oxide addition products thereof, addition products of from 2 to 200 mol of ethylene oxide on castor oil and/or hydrogenated castor oil, partial esters based on linear, branched, unsaturated or saturated C6-C22-fatty acids, ricinoleic acid and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose), mono-, di- and trialkyl phosphates and mono-, di- and/or tri-PEG-alkyl phosphates and salts thereof, polysiloxane/polyether copolymers (Dimethicone Copolyols), such as e.g. PEG/PPG-20/6 Dimethicone, PEG/PPG-20/20 Dimethicone, Bis-PEG/PPG-20/20 Dimethicone, PEG-12 or PEG-14 Dimethicone, PEG/PPG-14/4 or 4/12 or 20/20 or 18/18 or 17/18 or 15/15, polysiloxane/polyalkyl polyether copolymers and corresponding derivatives, such as e.g. Lauryl or Cetyl Dimethicone Copolyols, in particular Cetyl PEG/PPG-10/1 Dimethicone (ABIL® EM 90 (Evonik Degussa)), mixed esters of pentaerythritol, fatty acids, citric acid and fatty alcohol according to DE 11 65 574 and/or mixed esters of fatty acids having 6 to 22 carbon atoms, methylglucose and polyols, such as e.g. glycerol or polyglycerol, citric acid esters, such as e.g. Glyceryl Stearate Citrate, Glyceryl Oleate Citrate and Dilauryl Citrate.

Preferred emulsifiers used in the one embodiment are selected from those having a HLB-value of from 3 to 9, preferably 4 to 6 and more preferably about 5. Preferred emulsifiers are selected from polyglyceryl-4-diisostearat/polyhydroxysterat/sebacat (ISOLAN® GPS), PEG/PPG-10/1 dimethicone, (ABIL® EM 90), Polyglyceryl-4 Isostearate (ISOLAN® GI 34), Polyglyceryl-3 Oleate (ISOLAN® GO 33), Methylglucose Isostearate (ISOLAN® IS), Diisostearoyl Polyglyceryl-3 Dimer Dilinoleate (ISOLAN® PDI), Glyceryl Oleate (TEGIN® O V), Sorbitan Laurate (TEGO® SML), Sorbitan Oleate (TEGO® SMO V) and Sorbitan Stearate (TEGO® SMS). These preferred emulsifiers are available from Evonik Goldschmidt GmbH.

Anionic emulsifiers or surfactants can contain groups which confer solubility in water, such as e.g. a carboxylate, sulphate, sulphonate or phosphate group and a lipophilic radical. Anionic surfactants which are tolerated by skin are known in large numbers to the person skilled in the art and are commercially obtainable. In this context these can be alkyl sulphates or alkyl phosphates in the form of their alkali metal, ammonium or alkanolammonium salts, alkyl ether-sulphates, alkyl ether-carboxylates, acyl sarcosinates and sulphosuccinates and acyl glutamates in the form of their alkali metal or ammonium salts.

Cationic emulsifiers and surfactants can also be added. Quaternary ammonium compounds, in particular those provided with at least one linear and/or branched, saturated or unsaturated alkyl chain having 8 to 22 C atoms, can be employed in particular as such, thus, for example, alkylt-rimethylammonium halides, such as e.g. cetyltrimethylammonium chloride or bromide or behenyltrimethylammonium chloride, but also dialkyldimethylammonium halides, such as e.g. distearyldimethylammonium chloride.

Monoalkylamidoquats, such as e.g. palmitamidopropylt-rimethylammonium chloride, or corresponding dialkylami-doquats can furthermore be employed. Readily biodegradable quaternary ester compounds, which can be quaternized fatty acid esters based on mono-, di- or triethanolamine, can furthermore be employed. Alkylguanidinium salts can furthermore be admixed as cationic emulsifiers.

Typical examples of mild surfactants, i.e. surfactants which are particularly tolerated by skin, are fatty alcohol polyglycol ether-sulphates, monoglyceride sulphates, mono- and/or dialkyl sulphosuccinates, fatty acid isethionates, fatty acid sarcosinates, fatty acid taurides, fatty acid glutamates, ether-carboxylic acids, alkyl oligoglucosides, fatty acid glu-camides, alkylamidobetaines and/or protein-fatty acid condensates, the latter for example based on wheat proteins.

It is furthermore possible to employ amphoteric surfactants, such as e.g. betaines, amphoacetates or amphopropi-onates, thus e.g. substances such as the N-alkyl-N, N-dim-ethylammonium glycinates, for example coco-alkyldimethylammonium glycinate, N-acylaminopropyl-N, N-dimethylammonium glycinates, for example coco-acylamimopropyldimethylammonium glycinate, and 2-alkyl-3-carboxymethyl-3-hydroxyethylimidazolines having in each case 8 to 18 C atoms in the alkyl or acyl group, and coco-acylaminoethylhydroxyethylcarboxymethyl glyci-nate.

Of the ampholytic surfactants, those surface-active compounds which contain, apart from a C8/18-alkyl or -acyl group, at least one free amino group and at least one —COOH or —SO3H group in the molecule and are capable of formation of inner salts can be employed. Examples of suitable ampholytic surfactants are N-alkylglycines, N-alky-lpropionic acids, N-alkylaminobutyric acids, N-alkylimino-dipropionic acids, N-hydroxyethyl-N-alkylamidopropylgly-cines, N-alkyltaurines, N-alkylsarcosines, 2-alkylaminopropionic acids and alkylaminoacetic acids having in each case about 8 to 18 C atoms in the alkyl group. Further examples of ampholytic surfactants are N-coco-alkylaminopropionate, coco-acylaminoethylaminopropi-onate and 012/18-acrylsarcosine.

Preferred emulsifiers or surfactants used for formulating the composition are identical to those used in the production of the microbeads.

Many types of buffers or acids, as are well known to the skilled person, have been envisioned as suitable for the swelling and neutralizing of the crosslinked microbeads of one embodiment. In a preferred embodiment the buffer comprises a buffer with a pH value in the range of 2.0-8.0, preferably in the range of 5.0-7.5.

Optimally, a suitable buffer is chosen with a pH value, which results in that the crosslinked microbeads have a pH value as close to neutral as possible. In one embodiment, the buffer comprises a buffer with a pH value, which results in that the crosslinked microbeads have a pH value between 5.0 and 7.5. The buffer can be a phosphate buffer and/or a saline buffer. The crosslinked microbeads can be washed at least once with water, water and an acid, water and a phosphate buffer, water and a saline buffer, or water and a phosphate buffer and a saline buffer, with a pH value in the range of 2.0-8.0, preferably in the range of 5.0-7.5. The purifying step may comprise any separation technique known in the art, e.g. filtration, decantation, centrifugation and so on. It might be advantageous to combine one or more purifying steps with one or more neutralizing steps.

The purifying step can include dialyzing the crosslinked microbeads against de-ionized water using a dialysis membrane that allows free diffusion of molecules having a size less than 13,000 Daltons. Standard emollients used in cosmetic or personal care formulations as oil phase can be added. Such standard emollients are not hydrocarbons or aromatic hydrocarbons, especially not toluene, o-xylene, dodecane, heptane, isooctane or cetylethylhexanoate. Preferred emollients used in the one embodiment are selected from mono- or diesters of linear and/or branched mono- and/or dicarboxylic acids having 2 to 44 C atoms with linear and/or branched saturated or unsaturated alcohols having 1 to 22 C atoms, the esterification products of aliphatic difunctional alcohols having 2 to 36 C atoms with monofunctional aliphatic carboxylic acids having 1 to 22 C atoms, long-chain aryl acid esters, such as e.g. esters of benzoic acid with linear and/or branched C6-C22-alcohols, or also benzoic acid isostearyl ester, benzoic acid butyloctyl ester or benzoic acid octyldodecyl ester, carbonates, preferably linear C6-C22-fatty alcohol carbonates, Guerbet carbonates, e.g. dicaprylyl carbonate, diethylhexyl carbonate, longer-chain triglycerides, i.e. triple esters of glycerol with three acid molecules, at least one of which is longer-chain, triglycerides based on C6-C10-fatty acids, linear or branched fatty alcohols, such as oleyl alcohol or octyldodecanol, and fatty alcohol ethers, such as dialykl ether e.g. dicaprylyl ether, silicone oils and waxes, e.g. polydimethylsiloxanes, cyclom-ethylsiloxanes, and aryl- or alkyl- or alkoxy-substituted polymethylsiloxanes or cyclomethylsiloxanes, Guerbet alcohols based on fatty alcohols having 6 to 18, preferably 8 to 10 carbon atoms, esters of linear C6-C22 fatty acids with linear C6-C22-fatty alcohols, esters of branched C6-C13-carboxylic acids with linear C6-C22-fatty alcohols, esters of linear C6-C22-fatty acids with branched C8-C18- alcohols, in particular 2-ethylhexanol or isononanol, esters of branched C6-C13-carboxylic acids with branched alcohols, in particular 2-ethylhexanol or isononanol, esters of linear and/or branched fatty acids with polyhydric alcohols (such as e.g. propylene glycol, dimer diol or trimer triol) and/or Guerbet alcohols, liquid mono-/di-/triglyceride mixtures based on C6-C18-fatty acids, esters of C6-C22-fatty alcohols and/or Guerbet alcohols with aromatic carboxylic acids, plant oils, branched primary alcohols, substituted cyclohexanes, ring-opening products of epoxidized fatty acid esters with polyols and/or silicone oils or a mixture of two or more of these compounds. The emollient used is preferably not miscible with water without phase separation.

Monoesters which are suitable as emollients and oil components are e.g. the methyl esters and isopropyl esters of fatty acids having 12 to 22 C atoms, such as e.g. methyl laurate, methyl stearate, methyl oleate, methyl erucate, isopropyl myristate, isopropyl palmitate, isopropyl stearate, isopropyl oleate. Other suitable monoesters are e.g. n-butyl stearate, n-hexyl laurate, n-decyl oleate, isooctyl stearate, isononyl palmitate, isononyl isononanoate, 2-ethylhexyl laurate, 2-ethylhexyl palmitate, 2-ethylhexyl stearate, 2-hexyldecyl stearate, 2-octyldodecyl palmitate, oleyl oleate, oleyl erucate, erucyl oleate and esters which are obtainable from technical-grade aliphatic alcohol cuts and technical-grade aliphatic carboxylic acid mixtures, e.g. esters of unsaturated fatty alcohols having 12 to 22 C atoms and saturated and unsaturated fatty acids having 12 to 22 C atoms, such as are accessible from animal and plant fats. However, naturally occurring monoester and wax ester mixtures such as are present e.g. in jojoba oil or in sperm oil are also suitable. Suitable dicarboxylic acid esters are e.g. di-n-butyl adipate, di-n-butyl sebacate, di-(2-ethylhexyl) adipate, di-(2-hexyldecyl) succinate, di-isotridecyl azelate. Suitable diol esters are e.g. ethylene glycol dioleate, ethylene glycol di-isotridecanoate, propylene glycol di-(2-ethylhexanoate), butanediol di-isostearate, butanediol di-caprylate/caprate and neopentyl glycol di-caprylate. Fatty acid triglycerides can be used; as such, for example, natural plant oils, e.g. olive oil, sunflower oil, soya oil, groundnut oil, rapeseed oil, almond oil, sesame oil, avocado oil, castor oil, cacao butter, palm oil, but also the liquid contents of coconut oil or of palm kernel oil, as well as animal oils, such as e.g. shark-fish liver oil, cod liver oil, whale oil, beef tallow and butter-fat, waxes, such as beeswax, carnauba palm wax, spermaceti, lanolin and neat's foot oil, the liquid contents of beef tallow or also synthetic triglycerides of caprylic/capric acid mixtures, triglycerides from technical-grade oleic acid, triglycerides with isostearic acid, or from palmitic acid/oleic acid mixtures, can be employed as emollients (oil phase). Ghe organic or oil-phase can be mineral oil or TEGOSOFT® M. Preferably, the emulsifier is chosen from polyoxyethylene sorbitan fatty acid esters, sucrose fatty acid esters, sorbitan fatty acid esters, polysorbates, polyvinyl alcohol, polyvinyl pyrrolidone, gelatin, lecithin, poly-oxyethylene castor oil derivatives, tocopherol, tocopheryl polyethylene glycol succinate, tocopherol palmitate and tocopherol acetate, polyoxyethylene-polyoxypropylene co-polymers, or their mixtures.

The microbeads of one embodiment give access to the compositions of one embodiment comprising these microbeads. The compositions of one embodiment may comprise at least one additional component chosen from the group of emollients, emulsifiers and surfactants, thickeners/viscosity regulators/stabilizers, UV light protection filters, antioxidants, hydrotropic agents (or polyols), solids and fillers, film-forming agents, insect repellents, preservatives, conditioning agents, perfumes, dyestuffs, biogenic active compounds, moisturizers and solvents. The additional components might be inside and/or outside the microbeads. Preferably the additional ingredients are present in the composition of one embodiment outside or within the microbeads.

The composition of one embodiment can be an emulsion, a suspension, a solution, a cream, an ointment, a paste, a gel, an oil, a powder, an aerosol, a stick or a spray. The microbeads or the compositions of one embodiment may be used as a transdermal drug delivery system/vehicle. When applied topically the microbeads congregate in wrinkles and folds of the skin.

In another aspect, a method of producing a hydrogel comprising hyaluronic acid, or salt thereof, crosslinked with divinylsulfone (DVS) by (a) providing an alkaline solution of hyaluronic acid, or salt thereof;

(b) adding DVS to the solution of step (a), whereby the hyaluronic acid, or salt thereof, is crosslinked with the DVS to form a gel;

(c) treating the gel of step (b) with a buffer, wherein the gel swells and forms a hydrogel comprising hyaluronic acid, or salt thereof, crosslinked with DVS.

The hyaluronic acid, or salt thereof, has an average molecular weight of between 100 and 3,000 kDa, preferably between 500 and 2,000 kDa, and most preferably between 700 and 1,800 kDa. The initial concentration of hyaluronic acid, or a salt thereof, influences the properties of the resulting crosslinked gel, and of the swollen hydrogel. The alkaline solution comprises dissolved hyaluronic acid, or salt thereof, in a concentration of between 0.1%-40% (w/v). The pH value during the crosslinking reaction also influences the outcome, so in a preferred embodiment the invention relates to a method of the first aspect, wherein the alkaline solution comprises dissolved sodium hydroxide in a concentration of between 0.001-2.0 M. The concentration of the crosslinking agent can have a profound impact on the resulting gels. DVS is added to the solution of step (a) in a weight ratio of between 1:1 and 100:1 of HA/DVS (dry weight), preferably between 2:1 and 50:1 of HA/DVS (dry weight). An initial period of stirring during and/or immediately after adding the DVS to the HA-solution can be desirable to achieve satisfactory gelling. DVS is added with stirring to the solution of step (a), and wherein the solution temperature is maintained in the range of 5° C.-50° C., preferably in the range of 15° C.-40° C., more preferably in the range of 20° C.-30° C.; preferably the stirring is continued for a period of between 1-180 minutes. The DVS can be added without stirring to the solution of step (a).

The solution can be heated to a temperature in the range of 20° C.-100° C., preferably in the range of 25° C.-80° C., more preferably in the range of 30° C.-60° C., and most preferably in the range of 35° C.-55° C., and wherein the temperature is maintained in this range for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes; preferably without stirring.

It is advantageous to leave the gel standing at room temperature for a brief period after the crosslinking reaction has taken place. The gel is maintained for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes, at a temperature in the range of 0° C.-40° C., preferably in the range of 10° C.-30° C.

Many types of buffers, as are well known to the skilled person, have been envisioned as suitable for the swelling and neutralizing of the crosslinked gel of the invention. In a preferred embodiment the buffer comprises a buffer with a pH value in the range of 2.0-8.0, preferably in the range of 5.0-7.5. Optimally, a suitable buffer is chosen with a pH value, which results in that the swollen hydrogel has a pH value as close to neutral as possible. In a preferred embodiment, the buffer comprises a buffer with a pH value, which results in that the hydrogel has a pH value between 5.0 and 7.5. The buffer can be a phosphate buffer and/or a saline buffer. In the swelling step the buffer must have a sufficient volume for it to accommodate the swelling gel until the gel is fully swollen. The buffer in step (c) has a volume of at least 3 times the volume of the gel of step (b).

The swelling in step (c) is carried out at a temperature of between 20° C.-50° C. for a period of at least 5 minutes, preferably at least 10 minutes, 20 minutes, 30, 40, 50, 60, 70, 80, 90, 100, 110, 120, 130, 140, 150, 160, 170, or most preferably at least 180 minutes.

The hydrogel formed in step (c) can be washed at least once with water, water and a phosphate buffer, water and a saline buffer, or water and a phosphate buffer and a saline buffer, with a pH value in the range of 2.0-8.0, preferably in the range of 5.0-7.5.

It should be understood that various alternatives to the embodiments of the present exemplary system and method described herein may be employed in practicing the present exemplary system and method. It is intended that the following claims define the scope of the invention and that the system and method within the scope of these claims and their equivalents be covered thereby.

Figure 5:
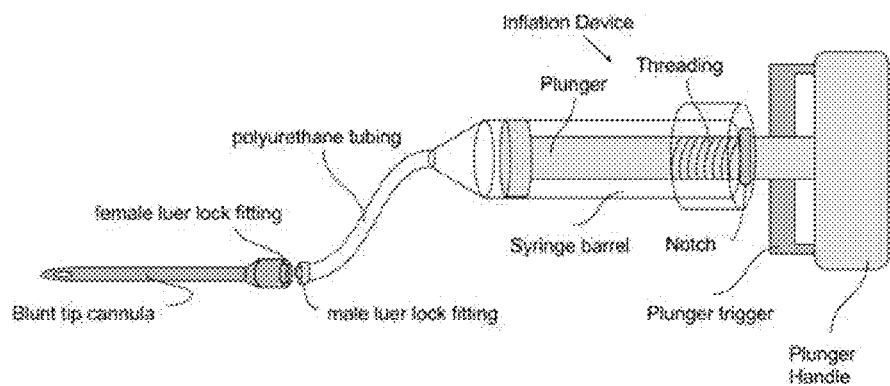
FIGS. 5-6 show exemplary injector configurations.
Figure 6:
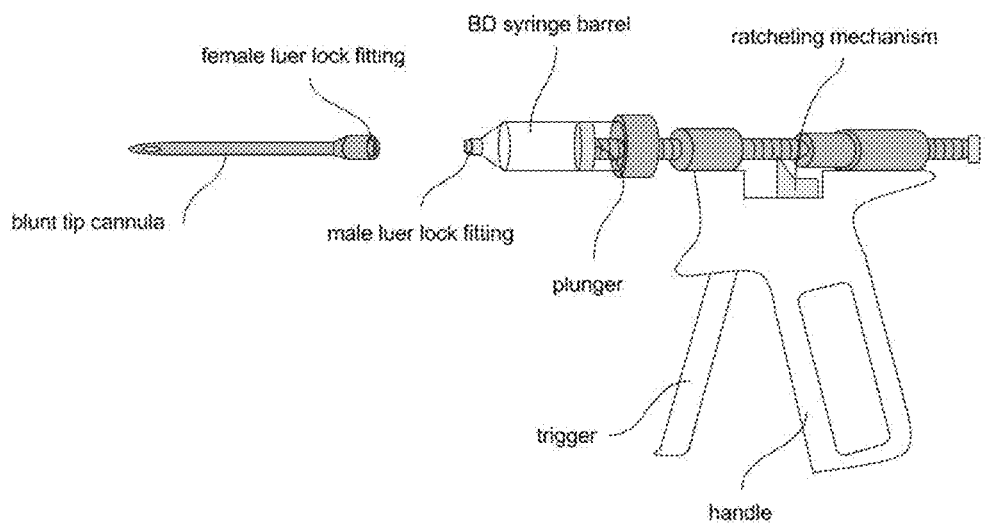

FIGS. 5-6 show exemplary injector configurations. The device of FIG. 5 can be human operated, computer operated, or a combination of human and computerized motor actuation. In FIG. 5, the injector includes an inflation device preloaded with a gel, and a blunt tip cannula. HA or PVA gel can be preloaded into the syringe barrel by a manufacturer by use of the male luer lock fitting of the polyurethane tubing that is coupled to the syringe barrel. For example, the manufacturer may choose to load the inflation device with gel by using a device compatible with the male luer lock fitting, such as a luer lock tip syringe. A blunt tip cannula with a compatible female luer lock fitting can be attached to the male luer lock fitting of the polyurethane tubing coupled to the inflation device. The user can manipulate the blunt tip cannula within a patient. The motor (or a person) can then grip the plunger handle and drive the plunger trigger toward the plunger handle, releasing the plungers locking mechanism, and allowing the plunger to travel along the syringe barrel. The plunger may travel along the length of the syringe barrel, extruding gel through the polyurethane tubing and out the cannula, until the notch on the plunger contacts the syringe barrel. Contact between the notch and the syringe barrel prevents further movement of the plunger along the length of the syringe barrel. Alternatively, instead of the user, a motor may drive the plunger into the syringe barrel by torqueing the plunger handle clockwise. Should the user or motor requires additional gel after expending all the gel in the inflation device, the user can remove the inflation device by the luer lock fittings from the cannula, dispose of it, and replace with a fresh preloaded inflation device.

FIG. 6 shows an exemplary injection gun fitted with a disposable syringe barrel preloaded with a gel, and a blunt tip cannula. Gel can be preloaded into the syringe barrel by the manufacturer by use of the male luer lock fitting of the polyurethane tubing that is coupled to the syringe barrel. For example, the manufacturer may choose to load the inflation device with gel by using a device compatible with the male luer lock fitting, such as a luer lock tip syringe.

The injection gun can be primed for use by gripping the handle, and pulling the plunger toward the user. For example, a BD syringe barrel preloaded with gel can be fitted at the end of the injection gun with the plunger inserted into the syringe barrel. A blunt tip cannula with a compatible female luer lock fitting can be attached to the male luer lock fitting of the BD syringe barrel. The user can hold the handle against the palm and extend fingers around the trigger. The user can manipulate the cannula within a patient and expel gel from the injection gun by actuating the trigger. Alternatively, a motor can be controlled by a processor to expel gel.

The injection gun operates by a ratcheting mechanism. The trigger actuates the ratcheting mechanism, pushing the plunger into the BD syringe barrel, expelling gel through the cannula. Each time the trigger is pulled, a controlled amount of gel is deposited. The user can operate the trigger until the gel is exhausted. Should the user require additional gel after expending all the gel in the BD syringe barrel, the user can remove the injection gun from the cannula, dispose of the syringe barrel, and replace with a fresh preloaded syringe barrel. The injection gun is then to be primed again with each injection. The injection gun can then reattach to the blunt tip cannula, and be ready for use.

Figure 7B:
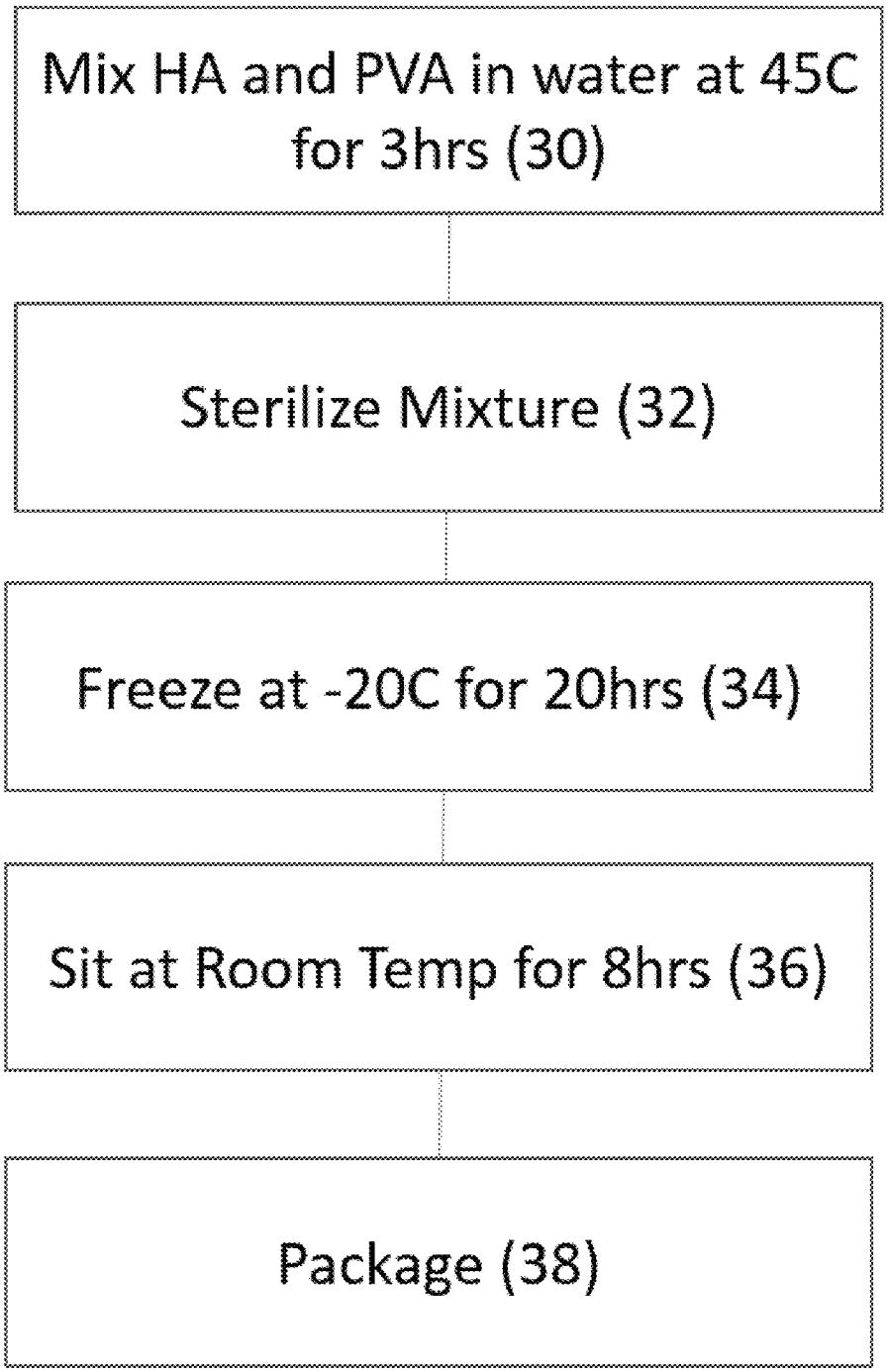

FIGS. 7A-7E show exemplary hydrogel fabrication processes that can produce large volume of gels for minimally invasive body augmentation. In FIG. 7A, hyaluronic acid (HA) and poly vinyl alcohol (PVA) are mixed with distilled water as a batch at 45° C. for about 3 hours (10). The mixture can have from about 95% to 80% PVA. PVA is a highly hydrophilic polymer with a chemical formula of $(C2H4O)n$ and the structural formula is $(-CH2CH(OH)-)n$. HA is an anionic, nonsulfated glycosaminoglycan distributed widely throughout connective, epithelial, and neural tissues. The mixture of HA-PVA is frozen at −20° C. for about 20 hours (12) and the batch is allowed to warm to room temperature for about 8 hours (14). In general, slower thawing leads to less leachable polymer. A more efficient gelation process can be achieved with decreasing thaw rates. The shear modulus of the hydrogel increases approximately linearly with decreasing log of the thawing rate. The batch is then sterilized and packaged (16). The sterilization can be done using an autoclave, which is a pressure chamber used to sterilize the HA-PVA gel by subjecting them to high pressure saturated steam at 121° C. (249° F.) for around two hours depending on the size of the load and the contents.

When PVA in aqueous solution (or in aqueous/DMSO mixtures) is heated to dissolution and then frozen and thawed repeatedly, it forms a highly elastic gel. The solgel transition forms a physically (not chemically) crosslinked polymer. Thus, the crosslinking that is achieved is thermoreversible. There is a dependence of the cryogel characteristics on the molecular weight of the uncrosslinked polymer, the concentration of the aqueous solution, temperature and time of freezing, the heating/cooling rates and the number of freeze-thaw cycles. Thus, there is a rich parameter space from which control of the mechanical properties of the PVA cryogels may be exercised. PVA cryogels exhibit very low toxicity (at least partially due to their low surface energy), contain few impurities and their water content can be made commensurate to tissue at 80 to 90 wt % and are thus generally considered to be fairly biocompatible.

In FIG. 7B, a similar process is done, but the sterilization is done prior to freezing. First, the HA and PVA are mixed with distilled water as a batch at 45° C. for about 3 hours (30) and sterilized in the autoclave oven (32). The result is frozen at −20° C. for about 20 hours (34) and the batch is allowed to warm to room temperature for about 8 hours (36). The batch is then packaged (38).

In FIG. 7C, the mixture of HA and PVA is done (50), and the mixture is sterilized (52). One or more cycles of freeze/thaw of the mixture is done (54), and the final thaw to room temperature is done and the product is then packaged as a sterile solution (56).

The swelling of PVA-HA gels at any time point decreases with increasing number of freeze-thaw cycles, indicating a densification of the PVA gel, most likely due to a higher crosslink density. In the long term, following gelation and under static conditions, the ultimate swelling ratio decreases while the modulus increases with time. In freeze-thaw processing, temperature is used to force a phase separation of the PVA solution, thus enhancing the gelation mechanism in the PVA (it should be noted that even at room temperature a solution of PVA begins to gel weakly over time). However, as HA is not affected by the number of freeze-thaw cycles, the presence of HA provides stability of the resulting gel.

FIG. 7D shows another process to form body augmentation hydrogel where the sterilization is done prior to freezing. First, the HA and PVA are mixed with distilled water as a batch at 45° C. for about 3 hours (70) and sterilized (72). One or more freeze/thaw cycles are done, where each time the mixture is frozen at −20° C. for about 20 hours and the batch is allowed to warm to room temperature for about 8 hours (74). The batch is then packaged (78).

Freeze/thaw cycling of PVA polymer in solution results in the formation of physical cross-linking (i.e. weak bonding through a nonpermanent "association" of the polymer chains). PVA hydrogels formed in this manner are thermoreversible and are termed "cryogels". In general, cryogels are solid elastomers containing over 80% water which are produced when solutions of higher molecular weight poly(vinyl alcohol) (PVA) of high degree of hydrolysis are subjected to one or more freeze-thaw cycles. Such cryogels are tough, slippery, elastomeric, resilient, insoluble in water below 50 degrees Celsius, and nontoxic. Freeze-thaw cycling of solutions of PVA polymer results in the formation of physical associations (i.e. weak bonding through an "association" of the polymer chains). PVA hydrogels formed in this manner are termed "cryogels" and are described, for example, in U.S. Pat. Nos. 6,231,605 and 6,268,405, 7,235,592, the entire contents of which are incorporated herein by reference. All references, patents, patent applications or other documents cited are hereby incorporated by reference herein in their entirety.

Importantly, the techniques utilized to create PVA cryogels do not require the introduction of chemical crosslinking agents or radiation. Cryogels are therefore easily produced with low impact on incorporated bioactive molecules. However, incorporated molecules are limited to those that can tolerate the freeze-thaw cycles required to make the gel. Thus the resulting material can contain bioactive components that will function separately following implantation. PVA cryogels are also highly biocompatible (as are PVA "thetagels," discussed below). They exhibit very low toxicity (at least partially due to their low surface energy), contain few impurities and their water content can be made commensurate to that of tissue at 80 to 90 wt %. In the preferred embodiment, HA is provided to cross-link with the PVA to provide additional biocompatibility and tissue like feeling to patients. HA is unique among glycosaminoglycans in that it is nonsulfated, forms in the plasma membrane instead of the Golgi, and can be very large, with its molecular weight often reaching the millions. HA is a polymer of disaccharides, themselves composed of D-glucuronic acid and D-N-acetylglucosamine, linked via alternating β-1,4 and β-1,3 glycosidic bonds. Hyaluronic acid can be 25,000 disaccharide repeats in length. Polymers of hyaluronic acid can range in size from 5,000 to 20,000,000 Da in vivo. The average molecular weight in human synovial fluid is 3-4 million Da Cross-linked versions of HA have been approved by the FDA for use as a dermal filler.

While the autoclave oven can be used to sterilize the composition, certain embodiments use e-beam for sterilization. Electron beam processing or electron irradiation is a process which involves using electrons, usually of high energy, to treat an object for a variety of purposes. This may take place under elevated temperatures and nitrogen atmosphere. The preferred embodiment uses e-beam for electron irradiation to provide sterilization and to cross-link polymers. Instead of ebeam, X-ray or suitable radiation types can be used to cross-link the PVA.

In FIG. 7E, the HA and PVA is mixed in water (80) and then ebeam is used to sterilize and crosslinking the HA-PVA mixture (82). Instead of ebeam, X-ray or suitable radiation types can be used to cross-link the PVA. Next, the system can optionally perform zero or more freeze/thaw cycles (84) before the mixture is packaged for use (86).

Poly(vinyl alcohol) useful is typically obtained as a dry powder or crystal, and can vary based upon several factors, including molecular weight, degree of polymerization, and degree of saponification (or hydrolysis). The molecular weight of the poly(vinyl alcohol) can vary, and can be chosen depending upon the particular application envisioned for the hydrogel. Generally, increasing the molecular weight of the poly(vinyl alcohol) increases the tensile strength and tensile stiffness, and thereby improves the properties of constructs such as vascular grafts, wherein increased strength is desirable. In other applications, such as a nerve bridge, lower molecular weight poly(vinyl alcohol) can be employed because lower tensile strength and lower tensile stiffness are desirable. Poly(vinyl alcohol) having an average molecular weight of from about 11,000 to 500,000 is preferred for practicing the invention. Poly(vinyl alcohol) having an average molecular weight of from about 85,000 to 186,000 is even more preferred for practicing the invention, especially when producing vascular grafts, and poly(vinyl alcohol) having an average molecular weight of from about 124,000 to 186,000 is especially preferred.

The water that is mixed with the HA-PVA preferably undergoes deionization, reverse osmosis and ultra-filtered to minimize the potential for any contamination of the HA-PVA. The concentration of the poly(vinyl alcohol) contributes to the stiffness of the hydrogel and can thus be chosen depending upon the stiffness of the material one desires to obtain. A more preferable mixture is obtained by mixing from about 10 to about 30 parts HA-PVA with from about 70 to about 90 parts by weight water, and an especially preferred mixture is obtained by mixing about 25 parts HA-PVA with about 75 parts by weight water. Isotonic saline (0.9% weight to volume in water) or an isotonic buffered saline may be substituted for water to prevent osmotic imbalances between the material and surrounding tissues if the hydrogel is to be used as a soft tissue replacement.

After the poly(vinyl alcohol) and water are mixed, it is often necessary to process the mixture to ensure that the poly(vinyl alcohol) is adequately solubilized. Suitable solubilization processes are generally known in the art and include, for example, heating the mixture, altering the pH of the mixture, adding a solvent to the mixture, subjecting the mixture to external pressure, or a combination of these processes. A method is to heat the mixture at a temperature of about 95° C.-120° C., for a period of time not less than 15 minutes and the one way of doing this, is an autoclave which also sterilizes the mixture before further processing.

After the mixture has been prepared, air bubbles that may have become entrapped in the mixture are removed. The solution can be allowed to sit for a period of time at an elevated temperature, to allow the air bubbles to rise out of solution. The mixture can also be placed in a sterile vacuum chamber for a short time to bring the bubbles out of solution. The mixture can also be centrifuged at an elevated temperature to bring the bubbles out of solution.

In yet another embodiment, a process produces the HA-PVA hydrogel in a two stage process. In the first stage a mixture of HA-PVA and water is placed in a mold, and repeatedly frozen and thawed, in cycles, until a suitable HA-PVA hydrogel is obtained. In a second stage, the HA-PVA hydrogel is removed from the mold, placed in water, and undergoes at least one other freeze-thaw cycle until desirable mechanical properties are achieved. In the first stage, a series of sequential steps is employed comprising: (i) mixing water with HA-PVA to obtain HA-PVA/water mixture; (ii) freezing the mixture; (iii) thawing the mixture; and (iv) repeating the freeze and thaw steps, as necessary, until an HA-PVA hydrogel having the desired physical properties is obtained. If necessary, the second stage may then be employed.

Figure 8A:
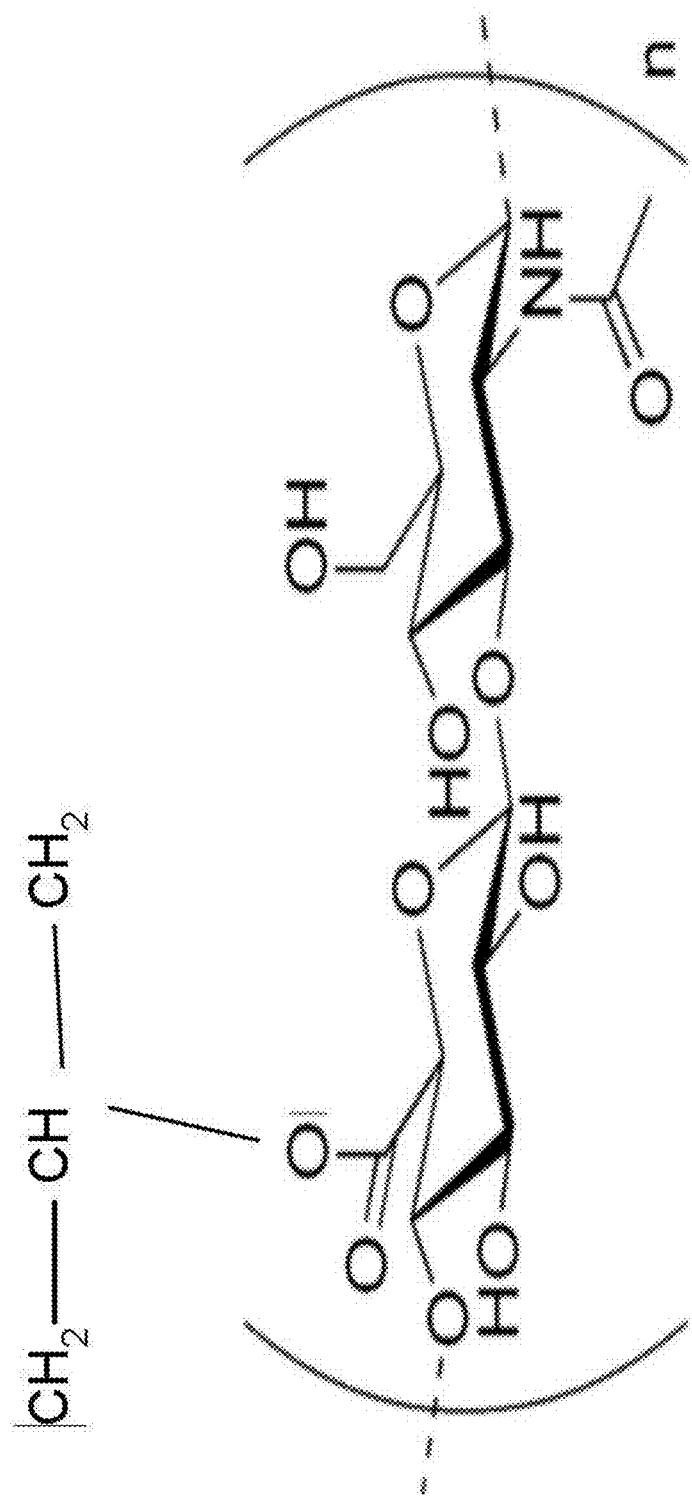
Figure 8B:
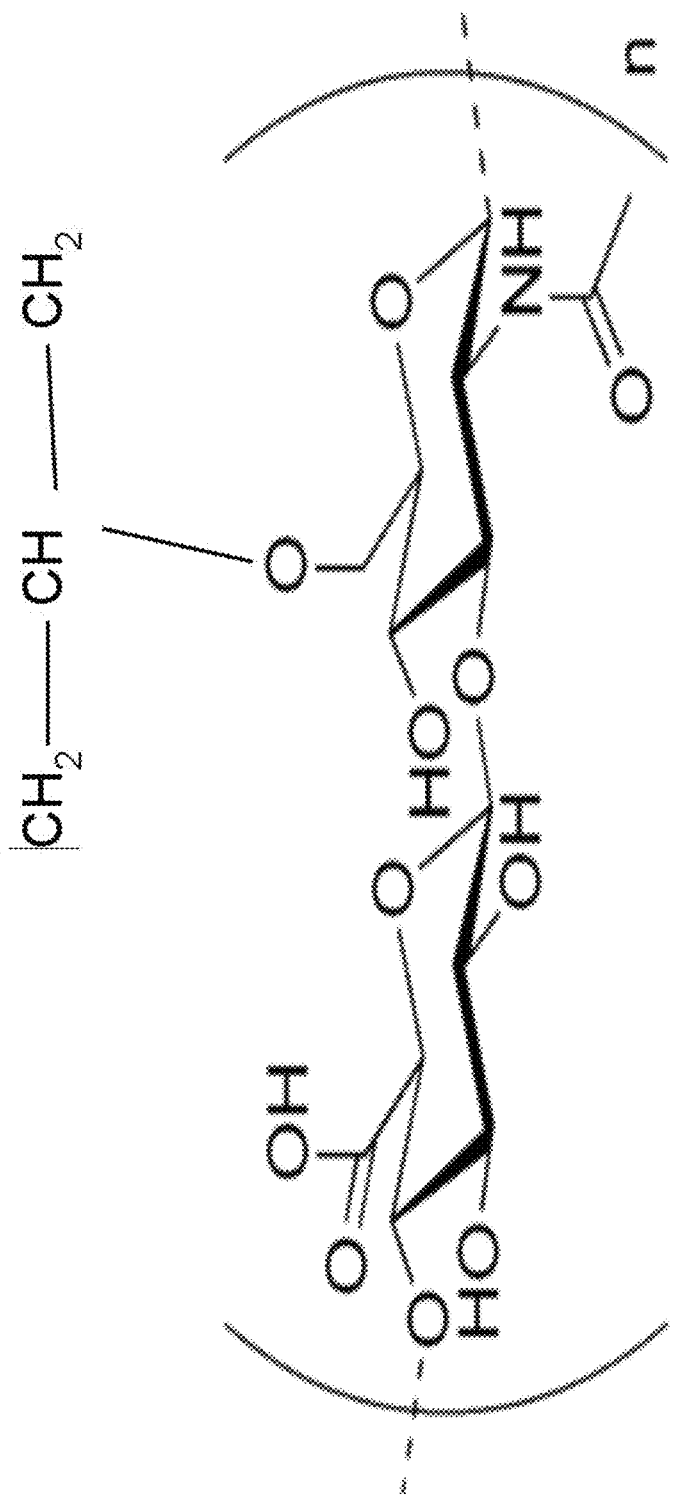
FIG. 8B shows ether bonding.

FIG. 8A shows exemplary HA-PVA bonding configurations with ester bonding, while FIG. 8B shows exemplary ether bonding configurations for HA-PVA. Crosslinks in HA-PVA gels may be either covalent (chemical) crosslinks or physical associations (physical). Covalent crosslinks are formed typically through chemical modification, or through irradiation. Physical associations may be formed via freeze-thaw cycling, dehydration or through controlled manipulation of the solubility of the vinyl polymer in a solvent (to produce a "thetagel"), disclosed in U.S. published patent application Ser. No. US20040092653 or by a combination of such methods. In general, the formation of a thetagel includes a step of mixing the vinyl polymer solution with a gellant, wherein the resulting mixture has a higher Flory interaction parameter than the vinyl polymer solution. In the present invention, both covalent and physical associations can be employed, in that a physically cross-linked precursor gel will be covalently crosslinked by irradiation. The use of irradiation to form covalent crosslinks has several advantages over chemical crosslinking Chemical crosslinking is often performed by the addition of a reactive metallic salt or aldehyde and subjecting the system to thermal radiation. For example, crosslinking may be performed by adding (di-)isocyanates, urea-/phenolic-melamine-resins, epoxies, or (poly-)aldehydes. However, the use of such reagents for chemical crosslinking can leave residues that decrease the biocompatibility of the PVA hydrogel.

Crosslink formation by irradiation of polymers in solution is a suitable method for the generation of hydrogels for biomedical use. Crosslinking via an ionization source provides adequate control of the reaction, a lower number of unwanted processes (e.g. homografting of monomer to the side of a polymer chain) and generates an end product suitable for use with little additional processing or purification. The irradiation and sterilization steps can often be combined.

Figure 9:
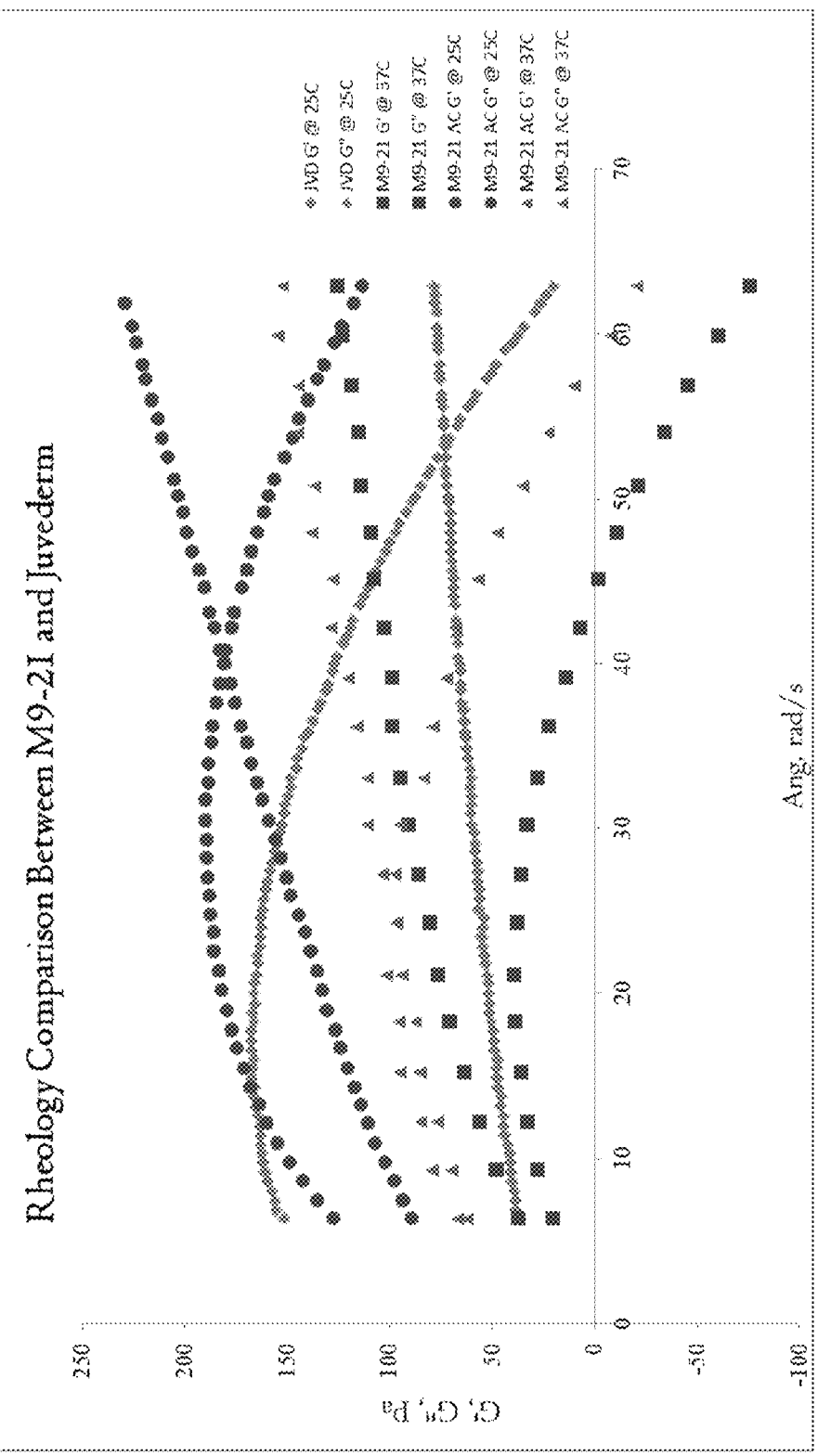
FIG. 9 show an exemplary comparison of one sample HA-PVA mixture to a commercial dermal filler.

The graph of FIG. 9 shows the temperature effect use on the sterilized gel at 25 C and 37 C. In general, high temperature reduces the elasticity and viscosity of the gel. FIG. 8's graph also illustrates differences between the sterilized PVA-HA gel and Juvederm gel at 25 C—the sterilized gel has higher viscosity and elasticity than the Juvederm gel at the same temperature 25 C. The unsterilized gel acts as a fluid.

Figure 10:
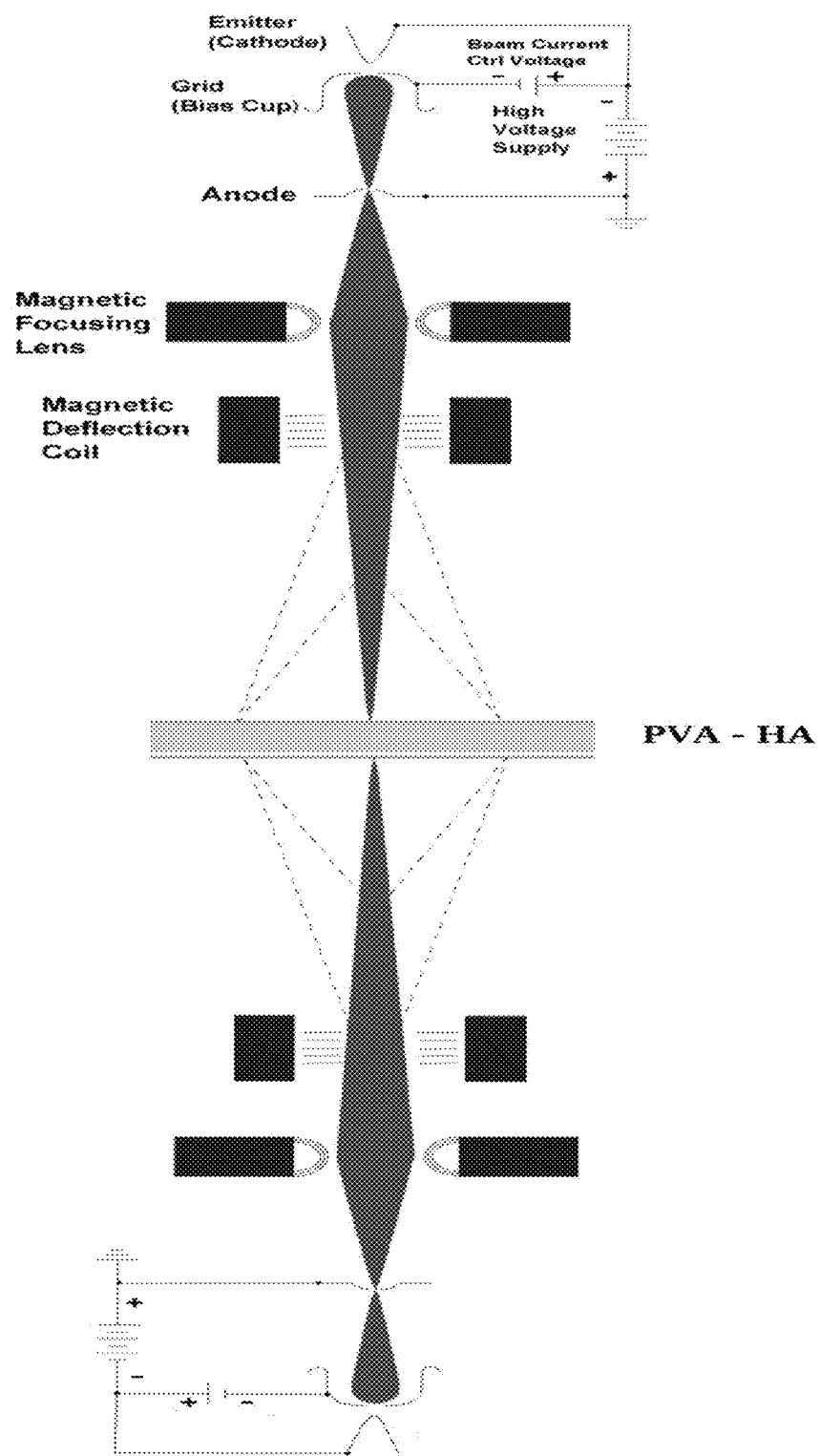
FIG. 10 shows an exemplary ebeam cross-linking system.

FIG. 10 shows a dual electron beam processing device are illustrated in the figure. In each portion, an electron gun (consisting of a cathode, grid, and anode) is used to generate and accelerate the primary beam. A magnetic optical (focusing and deflection) system is used for controlling the way in which the electron beam impinges on the HA-PVA mixture being processed. In operation, the gun cathode is the source of thermally-emitted electrons that are both accelerated and shaped into a collimated beam by the electrostatic field geometry established by the gun electrode (grid and anode) configuration used. The electron beam then emerges from the gun assembly through an exit hole in the ground-plane anode with an energy equal to the value of the negative high voltage (gun operating voltage) being applied to the cathode. This use of a direct high voltage to produce a high energy electron beam allows the conversion of input ac power to beam power at greater than 95% efficiency, making electron beam material processing a highly energy-efficient technique. After exiting the gun, the beam passes through an electromagnetic lens and deflection coil system. The lens is used for producing either a focused or defocused beam spot on the workpiece, while the deflection coil is used to either position the beam spot on a stationary location or provide some form of oscillatory motion. Dual Electron Beam Processing for high volume production doubles processing rates, ensures 100% system uptime, and virtually eliminates processing delays. The dual design minimizes stress via Gaussian electron waves for continuous and normalized distribution of energy. In one HA-PVA ebeam embodiment, an electron beam may be used on the material to induce effects such as chain scission (which makes the polymer chain shorter) and cross linking. The result is a change in the properties of the polymer which is intended to extend the range of applications for the material. The effects of irradiation may also include changes in crystallinity as well as microstructure. Usually, the irradiation process degrades the polymer. The irradiated polymers may be characterized using FTIR to confirm cross-linking presence.

The HA-PVA hydrogel can be irradiated while masked by a centrally placed aluminum disk to produce a step change in radiation dose between masked and exposed regions of the hydrogel. Shielding can be utilized to crosslink PVA disks with a stepped difference in radiation crosslinks. In one embodiment the shielding is made from a material with a uniform density and thickness. In other embodiments, different locations of the shield can have different thickness or different density and shaped to determine the area and degree of reduced radiation effectiveness. The material will block radiation (e-beam or gamma) in proportion to the thickness of the shielding piece. Following radiation crosslinking, the gel can be held at high temperature to melt-out the physical associations producing a PVA hydrogel having a gradient of crosslinks.

In one embodiment, a method of making a cross-linked vinyl polymer hydrogel includes providing a physically crosslinked HA-PVA hydrogel having a crystalline phase using freeze/thaw; exposing the physically crosslinked vinyl polymer hydrogel to an amount of ionizing radiation providing a radiation dose in the range of about 1-1,000 kGy effective to form covalent crosslinks; and removing the physical associations by exposing the irradiated vinyl polymer hydrogel to a temperature above the melting point of the physically associated crystalline phase to produce a cross-linked HA-PVA hydrogel. In preferred embodiments, the step of providing a physically associated vinyl polymer hydrogel having a crystalline phase includes the steps of providing a vinyl polymer solution comprising a vinyl polymer dissolved in a solvent; heating the vinyl polymer solution to a temperature elevated above the melting point of the physical associations of the vinyl polymer; inducing gelation of the vinyl polymer solution; and controlling the gelation rate to form physical associations in the vinyl polymer hydrogel. In preferred embodiments, the vinyl polymer is selected from the group consisting of poly(vinyl alcohol), poly(vinyl acetate), poly(vinyl butyral), poly(vinyl pyrrolidone) and a mixture thereof. Preferably, the vinyl polymer is poly(vinyl alcohol).

In preferred embodiments, the solvent of the vinyl polymer solution is selected from the group consisting of deionized water, methanol, ethanol, dimethyl sulfoxide and a mixture thereof. In preferred embodiments, the irradiated vinyl polymer hydrogel is immersed in a solvent is selected from the group consisting of deionized water, methanol, ethanol, dimethyl sulfoxide and a mixture thereof while is exposed to a temperature above the melting point.

In another aspect, systems and methods are disclosed for cosmetic augmentation of soft tissue using cross-linked HA-PVA that had been optimized for
1. ease of product delivery,
2. local tissue compliant,
3. greater cohesiveness to control migration of the implant material and
4. bio-degradation profile.

The use of a particularly cross linked HA, and cross linked by forming regions of interpenetrating network (IPN) of cross linked HA by further crosslinking them. The IPN configuration gives this cross linked HA those utilities unique for this cosmetic augmentation application. The IPN core is more resistance to biodegradation in a human body than the single cross-linked material normalized for the same cross linking level. Furthermore, varying physical properties that continuously changes radiating out from the core makes the polymer tough and at the same time compliant with the local tissue for better tissue/device biocompatibility and feels more natural to the touch.

The above HA cross linking method optimized for cosmetic augmentation in certain cases may need to control delivered pharmaceutical substances to modulate local tissue response to the polymer. The pharmaceutical component makes up the multi-phase mixture with the other phase being the cross linked HA polymer.

Implementations of the above aspects may include one or more of the following. The system is biocompatible and performs controlled drug releases at strategic timing to coincide with key physiological events. For example, a fast drug release profile and no delay would be well suited for the controlled release of an anesthetic such as lidocane to relieve acute pain experienced by the patient associated with the surgical procedure. The system is also capable of a medium release profile and a medium delay of a corticosteroid or steroid such as dexamethasone or triamcinolone to co-inside with a physiological inflammatory foreign body reaction. The system can also be customized to have a medium to slow release profile and a longer delay before starting the release of an antiproliferative drug such as paclitaxel, serolimas or 5-flourouracil to stop uncontrolled healing and excessive remodeling causing unsightly scar formation or capsular formation.

Another aspect of the present invention includes methods for optimizing biodegradation profiles and control migration of the implant material through the manipulation of various types molecular weight. The system optimizes biodegradation profiles and controls migration of the implant material. The system can be formulated around various types of molecular weights such as $M_n$, $M_w$ and $M_z$, and their polydispersity index (PDI) to optimize the biodegradation profiles to be from hypervolumic to isovolumic to hypovolumic.

The degradation reaction by oxygen derived free radical of HA was the results of studies using the HA present in synovial fluids. It showed that the HA was readily degraded by super oxide free radicals. This reaction is most favorable in the case of secondary free radicals. Neutrophils (polymorphonuclear leukocytes) produced the type of oxygen derived free radicals that allowed it phagocytotically consumed HA molecules. These WBC's are by far the exclusive destroyers of HA by oxygen-derived free radical mechanism. Thus, an aspect of this invention is to quench the effect of the free radical before it degrades the HA using free radical scavengers such as antioxidant vitamins.

Antioxidants are intimately involved in the prevention of cellular damage—the common pathway for cancer, aging, and a variety of diseases. Antioxidants are molecules which can safely interact with free radicals and terminate the chain reaction before vital molecules are damaged. The system can incorporate antioxidant enzymes to protect the longevity of HA. These enzymes can reduce the radicals and defend against ROS. They are: alpha-1-microglobulin, superoxide dismutases, catalases, lactoperoxidases, glutathione peroxidases and peroxiredoxins.

The system can apply different dose ranges to different areas of the same product at the same time so that the PVA-HA can have an inner core that is highly cross-linked while keeping the outer core with reduced HA crosslinking to provide enhanced bio-compatibility.

In various embodiments, cross-linked vinyl polymer hydrogels are produced by making a physically associated vinyl polymer hydrogel having a crystalline phase, exposing the physically associated vinyl polymer hydrogel to an amount of ionizing radiation providing a radiation dose that is effective to form covalent crosslinks, and removing physical associations by exposing the irradiated vinyl polymer hydrogel to a temperature above the melting point of the physically associated crystalline phase to produce a covalently cross-linked vinyl polymer. Typically the radiation dose is in the range of about 1-2,000 kGy. The physical properties of the produced hydrogel can be adjusted by varying controlled parameters such as the proportion of physical associations, the concentration of polymer and the amount of radiation applied. Such covalently crosslinked vinyl polymer hydrogels can be made translucent, preferably transparent, or opaque depending on the processing conditions. The stability of the physical properties of the produced vinyl polymer hydrogel can be enhanced by controlling the amount of covalent crosslinks. Preferably the fraction of physical associations removed ranges from about one tenth to substantially all of the physical associations. In other preferred embodiments, about 1-90% of the physical associations are removed.

In accordance with a preferred embodiment, the method of manufacturing a crosslinked vinyl polymer hydrogel includes the steps of providing the HA-PVA solution comprising a vinyl-HA polymer dissolved in a solvent; heating the vinyl-HA polymer solution to a temperature elevated above the melting point of the physical associations of the vinyl polymer, inducing gelation of the vinyl polymer solution; controlling the gelation rate to form crystalline physical associations in the vinyl polymer hydrogel, exposing the physically associated vinyl polymer hydrogel to a dose of ionizing radiation of about 1-1,000 kGy effective to produce covalent crosslinks and melting the vinyl polymer hydrogel in a solvent to remove substantially all or a fraction of the physical associations. In some preferred embodiments, the produced covalently crosslinked vinyl polymer hydrogel substantially lacks physical associations.

The desired physical property typically includes at least one of light transmission, gravimetric swell ratio, shear modulus, load modulus, loss modulus, storage modulus, dynamic modulus, compressive modulus, crosslinking and pore size.

In preferred embodiments, HA is mixed with the vinyl polymer, which is selected from the group consisting of poly(vinyl alcohol), poly(vinyl acetate), poly(vinyl butyral), poly(vinyl pyrrolidone) and a mixture thereof. Preferably the vinyl polymer is highly hydrolyzed poly(vinyl alcohol) of about 50 kg/mol to about 300 kg/mol molecular weight. In preferred embodiments, the vinyl polymer is highly hydrolyzed poly(vinyl alcohol) of about 100 kg/mol molecular weight. Typically the vinyl polymer solution is about 0.5-50 weight percent solution of poly(vinyl alcohol) based on the weight of the solution. In certain preferred embodiments, the vinyl polymer solution is about 1-15 weight percent. In other preferred embodiments, the vinyl polymer solution about 10-20 weight percent polyvinyl alcohol. The vinyl polymer, preferably poly(vinyl alcohol), can be isotactic, syndiotactic or atactic.

The solvent of the vinyl polymer solution is selected from the group consisting of deionized water (DI), methanol, ethanol, dimethyl sulfoxide and a mixture thereof. The solvent used in melting the vinyl polymer hydrogel to remove the physical associations is selected from the group consisting of deionized water, methanol, ethanol, dimethyl sulfoxide and a mixture thereof. In preferred embodiments, the same solvent is used for the vinyl polymer solution and for melting the vinyl polymer hydrogel to remove the physical associations.

In preferred embodiments, the ionizing radiation is X-ray, gamma radiation or beta particles (electron beam). In preferred embodiments, the total radiation dose is suitably 1-1,000 kGy, preferably 50-1,000 kGy, more preferably 10-200 kGy. The radiation dose rate is suitably about 0.1-25 kGy/min, preferably about 1-10 kGy/min. In preferred embodiments, the irradiation dose used is within 20% of the optimum irradiation dose, preferably within 10%, more preferably within 7% of the optimum irradiation dose. The optimum irradiation dose is specific to each polymer.

In preferred embodiments, the suitable polymer concentration of the hydrogel product to be irradiated can be optimized within the polymer concentration range flanking the maximum of a plot of intermolecular crosslinking yield v. polymer concentration or the minimum of a plot of irradiation dose v. polymer concentration, i.e. the point at which the slope of the plot is zero. Suitably, the polymer concentration falls in a range in which the intermolecular crosslinking yield or the irradiation dose is within 20% of the maximum or minimum value, respectively, preferably within 10%, more preferably within 7% of the value. Where the hydrogel comprises poly(vinyl alcohol), the hydrogel is suitably about 2 to about 35 weight percent poly(vinyl alcohol), preferably about 3.5 to about 30 weight percent poly(vinyl alcohol), more preferably about 5 to about 25 weight percent poly(vinyl alcohol), based on the weight of the composition.

After irradiation, the physical associations are removed by raising the temperature of the hydrogel above the melting point of the thermo-reversible physical associations. The required temperature depends on the melting point of the cross-links and is suitably about 0-100 degrees Celsius, preferably about 40-80 degrees Celsius. Preferably the irradiated gels are heated to high temperatures while they are immersed in solvent to allow dissolution and elution of the PVA chains "melted out" of the physical associations. The duration of the exposure to the elevated temperature can be adjusted to melt out all of the physical associations, or just a fraction of the physical associations.

The crosslinked vinyl polymer hydrogels of the present invention have an advantageous inherent material stability that is exhibited when the crosslinking is covalent chemical rather than physical. Forming covalent crosslinks by radiation rather than by chemical reagents avoids the potential problem of residual contaminants. For medical materials and articles of manufacture, both the irradiation and the sterilization steps can be performed simultaneously, simplifying manufacturing and reducing costs. The ability to control pore size by varying the degree of precursor gel physical crosslinking will be an advantage over other means of forming covalent vinyl polymer hydrogels.

The method can include timing the switch to match the typical time for development of tissue encapsulation (timing approach) or to have the encapsulation event itself trigger the switch (event triggered approach). FIG. 11 shows an exemplary hydrogel fabrication process that can produce large volume of gels with anti-inflammatory drugs or agents. In FIG. 11, the HA and PVA, along with an anti-inflammatory drug, are mixed with distilled water as a batch at 45° C. for about 3 hours (130) and sterilized in the autoclave oven (132). The result is frozen at −20° C. for about 20 hours (134) and the batch is allowed to warm to room temperature for about 8 hours (136). The batch is then packaged (138).

In another form of the present invention, a biodegradable layer can be formed on the HA-PVA material to act as a switch to turn on the release of an extracellular matrix (ECM) suppressing therapeutic agent (i.e. fluoroquinolone, glucosamine, diethylcarbamazine, etc.). Exemplary fluoroquinolones include ciprofloxacin, levofloxacin, and moxifloxacin. The drug can be ciprofloxacin which is an antibiotic in a group of drugs called fluoroquinolones. In one embodiment, the Cipro can be sprayed or otherwise atomized onto the implant surface. In another embodiment, the implant can be submersed in a solution with Cipro and a binder can be provided to bind the Cipro to the implant. Ciprofloxacin fights bacteria in the body. Ciprofloxacin is used to treat different types of bacterial infections. It is also used to treat people who have been exposed to anthrax. Other medications can be used, for example, leukotriene receptor antagonists, such as zafirlukast (Accolate®), montelukast (Singulair®), and pranlukast administered orally can moderate the capsular contracture. Other medications include antibiotics surrounding the implant Finally, textured implants have yielded a reduction in capsule formation.

Under the timing approach, a biodegradable layer can be coated on the therapeutic agent matrix that would degrade enough to allow therapeutic agent elution around 20 to 40 days, the typical time of tissue encapsulation of an implant. The layer could be configured to degrade in tissue and/or in blood. For the switch to be effective, it must effectively block ECM suppressing therapeutic agents from eluting for the duration of Encapsulation Development Time and then quickly turn on to fully elute a therapeutic agent to block proteoglycans (i.e. versican, decorin, biglycan), hyaluronan, inter-a-trypsin and/or collagen (types I and III) from being further synthesized and deposited. In this way significant ECM-related restenosis is prevented since proteoglycans and collagen are the dominant components of ECM. The ECM is responsible for the bulk of restenosis in the long term.

Since the typical ECM suppressing therapeutic agent (i.e. fluoroquinolone) is hydrophilic, a good solid barrier layer should be made of a hydrophobic or slightly hydrophobic substance to control the elution time and degradation time to better match the Encapsulation Development Time. This outer barrier layer of a more hydrophobic substance can be selected from polylactic acid (PLA), polyglycolic acid (PGA), a copolymer of PLA and PGA (PLGA), polycaprolactone (PCL), other biodegradable polyesters, polyamino acids, or other hydrophobic, biodegradable polymers.

Preferably, under the barrier layer and immediately adjacent to the therapeutic agent matrix layer another layer is provided that is instead slightly hydrophilic or closer in polarity to the therapeutic agent itself than the outer barrier layer. This middle layer is the key to the rapid, burst characteristic of therapeutic agent elution while the outer barrier layer is the key to the delayed onset characteristic of therapeutic agent elution. As an alternative or as a complement to providing a separate layer beneath the barrier layer that is opposite in polarity to the barrier layer and closer in polarity to the therapeutic agent, the material used to form the therapeutic agent soluble material can be provided in pockets distributed throughout the barrier layer. By interspersing the barrier matrix with pockets of a hydrophilic substance (i.e. dextran, heparin) a switch effect for accelerated barrier layer degradation and therapeutic agent elution can be better achieved. Upon a threshold level of water penetration into the barrier matrix containing the pockets, the pockets increase in pressure to the point where they burst to destroy the barrier structure. The pockets act as isolated reservoirs or oases for hydrophilic physiologic and other fluids that the barrier layer's base material does not readily accept. Although the biodegradation of the barrier layer may be directed by other means such as the emergence of a restenotic environment in which the barrier layer dissolves, the incorporation of pockets allows additional options for fine-tuning the timing of barrier degradation by also making it indirectly susceptible to hydrophilic fluids and environments.

If the therapeutic agent happens to be hydrophobic rather than hydrophilic the polarities (hydrophobicity and hydrophilicity) of the respective matrices, layers, and/or pockets should be reversed. The bottom line is that the outermost barrier layer is to be opposite in polarity to the therapeutic agent and the inner layer(s) or pocket(s) that are closer to the therapeutic agent are closer in polarity to the therapeutic agent. However, preferably the therapeutic agent itself is contained in a matrix that is opposite in polarity for stabilization. The design is sandwich-like in configuration with the outer barrier and the therapeutic agent matrix analogized to pieces of bread between the unique opposite polarity inner layer or pockets analogized to the meat. The inner opposite polarity layer is the trigger to burst elution because the therapeutic agent easily desolves within it suddenly and completely.

Under the event triggered approach, there are several ways to trigger the switch to allow therapeutic agent elution to occur upon tissue encapsulation of the implant implant:

1. First, the coating covering the therapeutic agent matrix is designed to immediately break down to allow therapeutic agent elution upon tissue encapsulation. This can be achieved by coating the therapeutic agent matrix with a slightly to hydrophobic, biodegradable outer barrier layer that breaks down quickly upon the presence of a slightly to very hydrophobic environment such as provided by restenotic material. A thin layer of wax or a fatty substance exemplify the type of coating to be used. Specific examples of these include lipoprotein, collagen, polyamino acids, PLA, PLGA, and polycaprolactone, 2. Second, the ECM suppressing therapeutic agent can be bound to a molecule that inactivates the therapeutic agent until ECM factors (i.e. collagen, proteoglycans) are present.

3. Third, the switch can be turned on by other factors accompanying tissue encapsulation or extracellular matrix thickening including: hormones, enzymes, and/or peptides, etc.

4. Fourth, pressure can be used to induce release of the therapeutic agent, i.e. by housing the therapeutic agent within a semi-permeable membrane that bursts or by including pressure-building pockets within a barrier layer.

5. Fifth, pH changes can be used to induce release of the therapeutic agent if the material retaining (i.e. coating or serving as a matrix for) the therapeutic agent is sensitive to acids or bases and degrades (in tissue or in blood) upon being subjected to acidic or basic environments. In one embodiment, the therapeutic agent is coated with a slightly hydrophobic, acid-sensitive layer of PLGA. Tissue encapsulation of the implant implant can trap the PLGA and the acids produced from PLGA degradation. Subsequently, the concentration of acids is dramatically increased which leads to rapid degradation of the PLGA itself.

This event triggered approach offers a high degree of control of therapeutic agent elution and/or activation. The onset of therapeutic agent elution and/or the catalyst for therapeutic agent activation is particularized to occur independently and exclusively on the implant localities encapsulated by tissue while the elution is restrained and/or the therapeutic agent remains dormant and inactive on the implant localities that are still bare and unencapsulated. Encapsulation rates vary between procedures, individuals, and implant localities. Therefore, event-triggered therapeutic agent control provides an individualized approach for enhanced accuracy, safety and effectiveness.

It is preferred that the dosage of the anti-restenosis therapeutic agent is higher at the ends of the implant to compensate more aggressive restenosis at the ends of the implant.

The AMF/ANF/AG material may take the form of a coating, a matrix, or an implant body so long as its structure and orientation are such that it can both facilitate endothelization and also delay the onset of therapeutic agent release, if therapeutic agents are used. Preferably, the AMF/ANF/AG material lasts for 15-30 days before it is fully degraded to expose the therapeutic agent underneath. However, it may work by fully degrading anywhere between 5-60 days. The AMF/ANF/AG material is preferably made of PGA or a copolymer of PGA-PLA. These are proven compounds used on DES as well as biodegradable sutures and are well documented for their compatibility with blood. PGA and PGA-PLA are especially well suited to degrade within 15-30 days. The delay time before onset of release of the ECM suppressing therapeutic agent (i.e. fluoroquinolone, glucosamine, diethylcarbamazine, etc.) is equal to the time it takes the AMF/ANF/AG material to fully degrade. This delay time is controlled by the exact chemical compounds used to create the coating and also the coating thickness. For example, since 50% PLA:50% PGA degrades more quickly than a 75% PLA:25% PGA mix, to obtain the same therapeutic agent release onset delay a thicker layer of 50% PLA:50% PGA would be used than if a 75% PLA:25% PGA mix were used. The AMF/ANF/AG material is preferably between 0.1 micron and 20 microns thick.

Alternatively, instead of PGA and/or PLA, the AMF/ANF/AG material can also preferably be made of poly (ethylene glycol) (PEG), also known as poly(ethylene oxide) (PEO) or polyoxyethylene (POE). Caprolactone (CPL) can also be used. CPL and PEG are elastomeric materials and if the AMF/ANF/AG medical device has elastomeric properties it will better conform to the natural shape of the lumen in which it is inserted or implanted. Elastomeric materials are better able to close gaps between an implant wall and a lumen wall. Avoiding incomplete apposition of the implant implants against the lumen wall reduces the formation of stagnant pockets in which a thrombus is more likely to develop. Metallic implant implants are typically stiff and cannot conform well to the lumen when the lumen is not smooth and uniform, as is often the case. However, an elastomeric coating upon non-elastomeric implant implants ameliorates this problem by flexing, bending, expanding, and contracting to occupy the differential spaces created by the nonconformity between the lumen wall and the implant implants. Alternatively, if the implant implants themselves are made of AMF/ANF/AG elastomeric materials they can directly model the irregular surface patterns of anatomic lumens.

The AMF/ANF/AG material can also be made out of biological molecules (biomolecules) such as collagen, fibrin, or fibrinogen. Various other substances that can be used to form the AMF/ANF/AG material are: phosphorylcholine, nitric oxide, high density lipoprotein, polyzene-F, PTFE polyetherester, hydroxyapatite, polyhydroxy-butyrate, polycaprolactone, polyanhydride, poly-ortho ester, polyiminocarbonates, polyamino acids, and polyvinyl alcohol.

Irrespective of the chemical components used to form the AMF/ANF/AG material, when used as a delay coating the AMF/ANF/AG material is preferably negatively charged and also preferably has a nitric oxide functional group. Thus, as the fibers degrade, nitric oxide is released. Within the bloodstream of the lumen occupied by the implant, the nitric oxide serves to further inhibit restenosis by preventing platelet aggregation and macrophage/leukocyte infiltration, reducing smooth muscle cell proliferation, and decreasing inflammation generally while aiding the healing process. An aligned coating with a nitric oxide group (ANO) on an implant (or other intravascular medical device) forms an artificial endothelium layer due to the smooth, streamlined surface the aligned fibers/grooves provide coupled with the ability of nitric oxide to prevent aberrations on this smooth surface as the fibers degrade.

The inventor recognizes the use of any biocompatible materials that can be formed into aligned nanofibers, aligned microfibers, or aligned grooves for the AMF/ANF/AG material used to form an implant, a coating, or a matrix for therapeutic agent(s). The present invention also recognizes the ability to use the AMF/ANF/AG material in conjunction with other coatings, layers, matrices, pores, channels, reservoirs, etc. to delay onset of the release of any therapeutic agent and/or to encourage structured (i.e. aligned) endothelization.

The present invention also teaches the criticality of matching the time period of delay prior to therapeutic agent release with the time it takes for the AMF/ANF/AG implant surface to become covered (i.e. encapsulated) by endothelization to a depth of approximately 0.1 mm. The artificial functional endothelium layer itself is a very thin (i.e. only one or a few cells thick). A thin layer does not burden the implant with unnecessary volume (i.e. on the periphery of a cross-section) that could make insertion and adjustment within the lumen more difficult. A thin layer also does not significantly reduce the inner diameter of the implant's lumen and therefore does not interfere with hemodynamics or obstruct blood supply to a treated area.

When the implant is not formed of a material (i.e. such as an elastomeric aligned material) that enables it to conform to the shape of a lumen surface, a thrombus is more likely to develop causing a localized inflammatory reaction. Also, when the implant doesn't conform well to the shape of a lumen, the process of restenosis cannot be effectively controlled. Although systematic therapeutic agents administered with BMS and therapeutic agents supplied by DES can slow or modulate the rate of ineffective restenosis they are not typically used to encourage a moderate amount of beneficial restenosis. Any restenosis that does occur in a vessel having an uneven surface with implant implants that inadequately conform to the natural cell and protein structure (and/or shape) of the vessel is likely to be uncontrollable and problematic. Smooth muscle cell migration and proliferation is likely to form the first tissue layer over the implant implants. In contrast, the present invention provides a preformed artificial functional endothelial layer to provoke a first in vivo layer of natural endothelial cell growth.

In some embodiments, a drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons. And, in some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

Moreover, the drug-retaining layer can comprise a polymer having ester-terminal groups. The polymer can have, for example, a molecular weight ranging from about 50 KDaltons to about 190 KDaltons, and a structure that remains at least substantially undegraded during the initial release of the drug, the structure comprising P—CO2R, where P is the polymer backbone and R is an alkyl group having from 1 to 4 carbons.

The coatings can be designed for a delay time before onset of the release of the drug and elution of the drug at a certain rate. In some embodiments, the drug-reservoir layer can further comprise an accelerant layer to accelerate the onset of elution. And, in some embodiments, the accelerant layer having a poly(lactic-co-glycolic acid) with acid terminal groups, a monomer ratio of lactic acid to glycolic acid that ranges from about 85:15 to about 50:50, and a molecular weight that ranges from about 90 KDaltons to about 120 KDaltons. In some embodiments, the accelerant layer can comprise a drug. The amount of drug in the accelerant layer can be 0, 5, 10, 15, 20, 25, 30, 35, 40, 45, 50, 60 percent, or any amount therein.

In fact, other variables can be used to design for a desired delay time and release rate of the drug. In some embodiments, for example, the thickness ratio of the drug-reservoir layer to the drug-containing layer can range from about 4:1 to about 10:1, and the miscibility of the drug in a coating can be preselected to affect the rate of drug migration. In some embodiments, the thickness of the coating can range from about 2 microns to about 9 microns. And, in some embodiments, the thickness ratio of the drug-retaining layer to the drug-containing layer ranges from about 4:1 to about 7:1.

As such, the teachings are generally directed to a method of inhibiting the formation of hyperproliferative tissue and promoting the formation of a functional endothelium after implantation of a medical device in a subject. The method can comprise applying a therapeutic coating on a medical device and implanting the device in the subject. In some embodiments, the coating can comprise a biodegradable drug-containing layer that (i) is positioned over a surface of a medical device and (ii) serves as a source of a drug that functions as an anti-proliferative agent in a subject; and, a biodegradable drug-reservoir layer positioned over a surface of the drug-containing layer and comprising a drug-retaining layer, the drug-retaining layer remaining void or substantially void of the drug at a time of implantation in the subject and functioning to retain and at least substantially block an initial release of the drug into the subject for a time sufficient to form a functional endothelium over the surface of the medical device, the functional endothelium providing a source of thrombomodulin to the subject.

In some embodiments, the drug-containing layer can be applied as a solvent mixture and the solvent can be dried after application using a substantially non-reactive heated gas. The drying can serve to at least substantially inhibit mobilization of the drug from the drug-containing layer during application of additional layers in the formation of the coating. In some embodiments, the drug-reservoir layer can comprise at least one sub-layer having a thickness of less than or equal to 3 microns, where a repeated application of the sub-layer can be used to form thicknesses of greater than 3 microns. In some embodiments, the accelerant layer can be positioned between the drug-containing layer and the remainder of the drug-reservoir layer, is more hydrophilic than the remainder of the drug-reservoir layer, and comprises at least one sub-layer having a thickness of less than or equal to 3 microns, where a repeated application the sub-layer is used to form thicknesses of greater than 3 microns. The application of the sub-layers can be used to at least substantially promote a retention of the drug in the drug-containing layer during formation of the coating when compared to such a coating without the application of the sub-layers.

The coatings taught herein can, in some embodiments, further comprise pockets of hydrophilic material in the drug-retaining layer, wherein the hydrophilic material comprises a component selected from the group consisting of dextran, heparin, ticlopidine, chlopidogrel, enoxaparin, dalteparin, hirudin, bivalirudin, argatroban, and danparoid. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, estradiol, and transcription factor E2F1.

In some embodiments, the teachings are directed to a medical device having a drug-retaining coating that at least substantially delays the initial elution of a drug for a time effective at forming a functional endothelium over a surface of the medical device. In some embodiments, the coatings are a switch for "turning on" drug elution at a desired time, where the switch can be programmed through coating design to elute at the desired time using the methods taught herein. In some embodiments, the coating can be designed to elute at a desired rate after the onset of elution.

In some embodiments, a coating "at least substantially delays the initial elution" includes, for example, where there is no measurable elution of drug for an initial period of time, or the elution of drug over the initial period of time is negligible or sufficiently retained, such that the desired effect that would be obtained in the absence of any drug elution is still obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. And, "a time effective at forming a functional endothelium over a surface of the medical device" can be, for example, any duration of time in which the elution of drug can be entirely or partially inhibited to allow for formation of an endothelium that provides a localized source of thrombomodulin where desired, in an area of an implant. In some embodiments, the terms "block", "delay", and "retain" can be used interchangeably.

The coating can comprise a drug-containing layer applied over a surface of the medical device. In some embodiments, the drug-containing layer can be 100% drug. In some embodiments, the drug-containing layer can comprise 5, 10, 15, 20, 25, 30, 35, 40, 45, 50, 55, 60, 65, 70, 75, 80, 85, 90, 95, 99, 100 percent drug, or any amount therein.

The surface of the medical device can include any surface of a medical device, such as an implanted medical device. The surface may be, for example, a breast or buttock implant, in some embodiments. The drug-containing layer can be used to provide a drug that functions as an anti-proliferative agent; and, a drug-reservoir layer can be applied over the drug-containing coating.

In some embodiments, the HA-PVA hydrogel can comprise a drug-retaining layer that is void or substantially void of the drug at a time of implantation in a subject. A layer can be considered "substantially void" of the drug where the layer has an almost immeasurable amount of drug in the layer, or the amount is so small that the effect on the delay in onset of drug elution is still controllable using the coatings and methods taught herein. In some embodiments, a layer is substantially void of the drug, where the amount of drug is negligible or sufficiently small, such that the desired effect of the delay in the onset of elution would be obtained to a desired degree, wherein the degree can be 5, 10, 15, 20, 25, 30, 35, 40, 45, 50, 55, 60, 65, 70, 75, 80, 85, 90, 95, 99, 100 percent, or any amount therein, of the desired effect. In some embodiments, a layer is substantially void of drug where the drug composes less than 2.0, 1.0, 0.8, 0.6, 0.5, 0.4, 0.3, 0.2, 0.1, 0.09, 0.08, 0.07, 0.05, 0.03, 0.01, 0.001 percent of the layer, or any amount therein.

The teachings are naturally directed to include a therapeutic coating that promotes formation of a functional endothelium on a medical device. The coating comprises a biodegradable drug-containing layer that is positioned over a surface of a medical device and serves as a source of a drug that functions as an anti-proliferative agent in a subject. The coating can also comprise a biodegradable drug-reservoir layer positioned over a surface of the drug-containing layer. The drug-reservoir layer can comprise a drug-retaining layer, wherein the drug-retaining layer can be void or substantially void of the drug at a time of implantation in the subject and function to retain and at least substantially block an initial release of the drug into the subject for a time sufficient to form a functional endothelium over the surface of the medical device. As discussed, the functional endothelium can provide a beneficial source of thrombomodulin to the subject to an area affected by a medical device.

It should be appreciated that, in the embodiments taught herein, the drug may be selected by its miscibility in a preselected polymer matrix. For example, the drug may be selected because it is at least substantially miscible in the drug-reservoir layer in order to retain the drug for a desired amount of time. Or, the drug may be miscible to a preselected degree, an amount sufficient to facilitate a desired retention time of the drug. A desired retention time is facilitated, for example, in a case where a functional endothelium has formed to a desired extent. It should be appreciated that the desired retention time is facilitated where the retention time is modulated to a desired amount, and the modulation of the time can include an increase or a decrease in the retention time through altering one or more coating variables, as described herein. One of skill should appreciate, for example, that miscibility of the drug with the polymer is a variable that can modulate an affinity of the drug for the polymer, in some embodiments, thus affecting retention time.

In some embodiments, the drug and polymer are mixed or blended in solution, and one skill will appreciate that the mixes or blends can be considered substantially miscible, for example, where they mix or blend homogeneously in the desired proportions of drug to polymer, at least for the purposes of the teachings provided herein. In contrast, the mixes or blends may be considered immiscible, at least for the purposes of the teachings provided herein, where the mix or blend of polymer and drug is not homogeneous in the mix or blend in the proportions desired. In some embodiments, a drug can be considered substantially miscible in a polymer, where a homogeneous, saturated solution comprising the drug in a solvent spreads on a layer of the polymer, such that (i) the solution of the drug in the solvent has a contact angle of greater than 90 degrees on the surface of the polymer; and (ii) the layer of the polymer was formed used the same solvent. In some embodiments, the drug is substantially miscible in the polymer where the surface tension of the drug and the surface tension of the polymer are the same or similar when compared using the same solvent. A surface tension is the same, where the difference is not statistically significant, and similar, where the surface tension does not vary by more than 1, 2, 3, 4, 5, 10, 15, 20, 25, or 30 percent, in some embodiments. It should be appreciated, however, that any method known to one of skill can be used to determine the relative degree of miscibility and affinity between the drug and the polymer.

In some embodiments, the retention time of a drug can be a time sufficient amount, or an otherwise desired amount of time, chosen based on any number of parameters recognized and known to one of skill in the art of drug elution from implanted medical devices. Such parameters can vary the desired amount of time based on, for example, type of implant, location of implant, construction of implant, selection of drug, desired effect, and the like.

The polymeric compositions taught herein include any desired polymer, combination of polymers, copolymers and agents known to one of skill to be useful as a medical device, or coating, as taught herein. These polymers can be biodegradable due to their labile nature, such as the labile nature of the ester groups that are present in some polymers. In some embodiments, these compositions can be designed such that they can be broken down, absorbed, resorbed and eliminated by a mammal. As such, the compositions can be used, for example, to form medical articles and coatings.

The terms "combine," "combined," and "combining" all refer to a relationship between components of a composition and include blends, mixtures, linkages, and combinations thereof, of components that form the compositions. The linkages can be connections that are physical, chemical, or a combination thereof. Examples of physical connections include, but are not limited to, an interlinking of components that can occur, for example, in interpenetrating networks and chain entanglement. Examples of chemical connections include, but are not limited to, covalent and noncovalent bonds. Covalent bonds include, but are not limited to, simple covalent bonds and coordinate bonds. Non-covalent bonds include, but are not limited to, ionic bonds, and intermolecular attractions such as, for example, hydrogen bonds and attractions created by induced and permanent dipole-dipole interactions.

Compositions that are selected for an in vivo use should meet particular requirements with regard to physical, mechanical, chemical, and biological properties of the compositions. An example of a physical property that can affect the performance of a biodegradable composition in vivo is water uptake. An example of a mechanical property that can affect the performance of a composition in vivo is the ability of the composition to withstand stresses that can cause mechanical failure of the composition such as, for example, cracking, flaking, peeling, and fracturing. An example of a chemical property that can affect performance of a biodegradable composition in vivo is the rate of absorption of the composition by a subject. An example of a biological property that can affect performance of a composition in vivo is the bioactive and/or biobeneficial nature of the composition, While not intending to be bound by any theory or mechanism of action, water uptake by a composition can be an important characteristic in the design of a composition. Water can act as a plasticizer for modifying the mechanical properties of the composition. Control of water uptake can also provide some control over the hydrolysis of a coating and thus can provide control over the degradation rate, absorption rate, and the agent release rate of a medical article or coating in vivo, such as for the release of a drug. In some embodiments, an increase in hydrolysis can also increase the release rate of an agent by creating channels within a medical article or coating that can serve as transport pathways for diffusion of the agents from the composition. The terms "subject" and "patient" can be used interchangeably and refer to an animal such as a mammal including, but not limited to, non-primates such as, for example, a cow, pig, horse, cat, dog, rat, and mouse; and primates such as, for example, a monkey, or a human.

In some embodiments, the compositions may be used, for example, to form medical articles and coatings (i) that have sufficient mechanical properties for applications that can benefit from biodegradable polymers, (ii) that can release agents substantially free of additional molecules derived from a polymeric carrier, (iii) that can be designed to have a predetermined release rate and absorption rate; and (iv) that can be combined with agents that are not only bioactive and/or biobeneficial but also control a physical property and/or a mechanical property of a medical article or coating formed from the polymer.

A polymer or coating can be "biodegradable," for example, when it is capable of being completely or substantially degraded or eroded when exposed to an in vivo environment or a representative in vitro environment. A polymer or coating is capable of being degraded or eroded when it can be gradually broken-down, resorbed, absorbed and/or eliminated by, for example, hydrolysis, enzymolysis, oxidation, metabolic processes, bulk or surface erosion, and the like within a subject. It should be appreciated that traces or residue of polymer may remain on the device, near the site of the device, or near the site of a biodegradable device, following biodegradation. The terms "bioabsorbable" and "biodegradable" are used interchangeably in this application. The polymers used in the teachings herein may be biodegradable and may include, but are not limited to, condensation copolymers. In some embodiments, the drug-containing layer can comprise a poly(lactic-co-glycolic acid), a monomer ratio of lactic acid to glycolic acid ranges from about 85:15 to about 50:50, and a molecular weight ranging from about 90 KDaltons to about 160 KDaltons.

Biodegradable polymers can be used, and biodegradable polymers should be selected according to their behavior and hydrolysis in vivo. In some embodiments, the number average molecular weight of the polymer fragments should be at or below about 40,000 Daltons, or any range therein. In some embodiments, the molecular weight of the fragments range from about 300 Daltons to about 40,000 Daltons, from about 8,000 Daltons to about 30,000 Daltons, from about 10,000 Daltons to about 20,000 Daltons, or any range therein. The molecular weights are taught herein as a number average molecular weight.

Examples of polymers that can be used in some embodiments include, but are not limited to, poly(acrylates) such as poly(butyl methacrylate), poly(ethyl methacrylate), poly(hydroxylethyl methacrylate), poly(ethyl methacrylate-co-butyl methacrylate), copolymers of ethylene-methyl methacrylate; poly(2-acrylamido-2-methylpropane sulfonic acid), and polymers and copolymers of aminopropyl methacrylamide; poly(cyanoacrylates); poly(carboxylic acids); poly(vinyl alcohols); poly(maleic anhydride) and copolymers of maleic anhydride; fluorinated polymers or copolymers such as poly(vinylidene fluoride), poly(vinylidene fluoride-co-hexafluoro propene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); poly(propylene) co-poly(ether-esters) such as, for example, poly(dioxanone) and poly(ethylene oxide)/poly(lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL), copolymers of acrylonitrile-styrene, ABS resins, and copolymers of ethylene-vinyl acetate; poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and derivatives, analogs, homologues, congeners, salts, copolymers and combinations thereof. In some embodiments, other polymers may be selected such that they specifically exclude any one or any combination of these polymers.

In some embodiments, the coatings can comprise one or more biodegradable polymers. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, or combinations thereof. In some embodiments, the biodegradable polymers include, but are not limited to, polyesters, poly(ester amides); amino acids; PEG and/or alcohol groups, polycaprolactones, poly(L-lactide), poly(D,L-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g. PEO/PLA), polyalkylene oxalates, polyphosphazenes, PHA-PEG, and any derivatives, analogs, homologues, salts, copolymers and combinations thereof. In some embodiments, the polymers can include poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof. In some embodiments, the polymers are selected such that they specifically exclude any one or any combination of these polymers.

In some embodiments, the polymers can be chemically connected by covalent bonds. In some embodiments, the polymers can be chemically connected to by non-covalent bonds such as, for example, by ionic bonds, inter-molecular attractions, or a combination thereof. In some embodiments, the polymers can be physically connected. In some embodiments, the polymers can be chemically and physically connected. Examples of ionic bonding can include, but are not limited to, ionic bonding of an anionic site to a cationic site between polymers. In some embodiments, an anionic site can be bound to a quaternary amine. Examples of inter-molecular attractions include, but are not limited to, hydrogen bonding such as, for example, the permanent dipole interactions between hydroxyl, amino, carboxyl, amide, and sulfhydryl groups, and combinations thereof. Examples of physical connections can include, but are not limited to, interpenetrating networks and chain entanglement. The polymers can also be blended or mixed.

The behavior of the polymer matrix can be changed through selection of any number of factors that provide the desired drug elution, chemical and physical characteristics of the coatings taught herein. For example, the terminal end groups can be designed to contribute to imparting such characteristics in the polymers. A more hydrophilic end-group can increase the rate of ingress of water, for example, and likewise increase the rate of hydrolysis of the polymer chains, at least in some embodiments. Likewise, a less hydrophilic group can deter in the ingress of water, and slow the rate of hydrolysis, at least in some embodiments.

It should be appreciated that a polymer can be selected to have acid terminal end-groups, hydroxyl terminal end-groups, alkyl-ester end-groups, or a combination thereof. Moreover, a polymer layer can be created using sub-layers, where the layer can have a sub-layer having acid groups, a sub-layer having hydroxyl groups, a sub-layer having ester end-groups, or a combination thereof. In fact, the construction of the layers and sub-layers can be designed based on thickness ratios to design a coating that provides a desired characteristic or set of characteristics including, but not limited to, drug-retention time, a desired rate of hydrolysis, a desired glass transition temperature, a desired drug-elution rate, a desired toughness, a desired elasticity, a desired modulus, or a combination thereof.

Molecular weights can also be selected for the polymer in a particular layer or set of layers in the coating, as a mixture of molecular weights in a particular layer or set of layers, or as a set of sub-layers, where each layer in the sub-layer can have an independently selected molecular weight, mixture of molecular weights, or a combination thereof, where the molecular weight or mixture of molecular weights can be the same or different for each sub-layer. And, in many embodiments, a desired characteristic is that the polymers have a structure that remains at least substantially undegraded during the initial release of the drug. In some embodiments, for example, the drug-retaining layer can comprise a polymer having ester-terminal groups.

In some embodiments, the drug-retaining layer can comprise a poly(lactic-co-glycolic acid) having ester terminal groups, a monomer ratio of lactic acid to glycolic acid ranging from about 85:15 to about 50:50, and a molecular weight ranging from about 90 KDaltons to about 160 KDaltons.

The molecular weights can be selected and tailored for a particular polymer selection and for a particular coating layer and purpose. For example, the polymer can have a molecular weight ranging from about 50 KDaltons to about 190 KDaltons, from about 50 KDaltons to about 190 KDaltons, from about 50 KDaltons to about 180 KDaltons, from about 60 KDaltons to about 170 KDaltons, from about 70 KDaltons to about 160 KDaltons, from about 80 KDaltons to about 150 KDaltons, from about 90 KDaltons to about 140 KDaltons, from about 90 KDaltons to about 160 KDaltons, from about 100 KDaltons to about 160 KDaltons, or any range therein.

Without intending to be bound by any theory or mechanism of action, in some embodiments, the drug-reservoir layer is initially implanted in a "drug-absorbing" state and is later transformed into a "drug-release" state over time due to changes in the physical and chemical structure across the coating in vivo. In the drug-absorbing state, the drug-reservoir layer has the highest affinity for the drug. In the drug-release state the drug-reservoir layer has a substantially lower affinity for the drug. The drug can have the highest solubility in the drug-reservoir layer in the drug-absorbing state and in the drug-release state, the drug can have a substantially lower solubility in the drug-reservoir layer. In some embodiments, the drug-absorbing state can reflect the state in which the glass transition temperature (Tg) of the drug-reservoir layer is higher than the temperature of the surrounding tissue/fluid, and the drug-release state can reflect the state at which the Tg of drug-reservoir layer is equal to or less than that of surrounding tissue/fluid. In some embodiments, coating has a Tg above the surrounding tissue temperature of 37 degrees C.

The polymer end-groups can have any structure known to one of skill that will provide the desired polymer characteristics for a particular coating layer or set of layers. In some embodiments, the end-group can be an ester-terminal group. For example, the polymer structure can comprise P—CO2R, where P is the polymer backbone and R can be an alkyl group having from 1 to 4 carbons, from 1 to 20 carbons, from 2 to 12 carbons, from 1 to 10, from 2 to 8, from 1 to 6 carbons, from 1 to 5 carbons, or any range therein. In some embodiments, R can be any end-group known to one of skill, with the limitation that R cannot affect usefulness of the polymer, for example, the ability of the polymer to be applied as a coating on a desired medical device. In some embodiments, R can be saturated, unsaturated, aromatic, aliphatic, or any combination thereof.

In some embodiments, an R group can be a H; an aliphatic hydrocarbon group such as, for example, an alkyl, alkenyl, or alkynyl group; an aromatic group such as, for example, an aryl, aralkyl, aralkenyl, of aralkynyl group; various other groups as defined herein, or a combination thereof.

In some embodiments, the aliphatic radicals have from about 1 to about 50 carbon atoms, from about 2 to about 40 carbon atoms, from about 3 to about 30 carbon atoms, from about 4 to about 20 carbon atoms, from about 5 to about 15 carbon atoms, from about 6 to about 10 carbon atoms, and any range therein. In some embodiments, the aromatic radicals have from about 4 to about 200 carbon atoms, from about 6 to about 150 carbon atoms, from about 12 to about 120 carbon atoms, from about 18 to about 90 carbon atoms, from about 24 to about 60 carbon atoms, and any range therein.

The term "alkyl" refers to a straight-chained or branched hydrocarbon chain. Examples of alkyl groups include lower alkyl groups such as, for example, methyl, ethyl, n-propyl, iso-propyl, n-butyl, iso-butyl, t-butyl or iso-hexyl; upper alkyl groups such as for example, n-heptyl, n-octyl, isooctyl, nonyl, decyl, and the like; lower alkylene such as, for example, ethylene, propylene, propylyne, butylenes, butadiene, pentene, n-hexene and iso-hexene; and upper alkylene such as, for example, n-heptene, n-octene, iso-octene, nonene, decene, and the like. Persons of ordinary skill in the art are familiar with numerous straight-chained and branched alkyl groups, which are within the scope of the present invention. In addition, such alkyl groups may also contain various substituents in which one or more hydrogen atoms is replaced by a functional group, or the alkyl groups can contain an in-chain functional group. The phrase "straight-chained or branched" includes any substituted or unsubstituted acyclic carbon-containing compounds including, but not limited to, alkanes, alkenes and alkynes.

The term "alkenyl" refers to a straight-chained or branched hydrocarbon chain including at least one alkene functionality. The term "alkynyl" refers to a straight-chained or branched carbon-containing chain including at least one alkyne functionality. The term "aryl" refers to a carbon-containing ring bearing a system of conjugated double bonds often comprising at least six π (pi) electrons. Examples of aryl groups include, but are not limited to, phenyl, naphthyl, anysyl, toluoyl, xylenyl, and the like. The term "aralkyl" refers to an alkyl group substituted with at least one aryl group. The term "aralkenyl" refers to an alkenyl group substituted with at least one aryl group.

A radical is "straight-chained" when it has less than 0.1 mole percent of side chains having 1 or more carbon atoms.

In some embodiments, a radical is straight-chained if it has less than 0.01 mole percent of such side chains. In some embodiments, a radical is straight-chained if it has less than 0.001 mole percent of such side chains. A radical is "branched" when it has more than 0.1 mole percent of side chains having 1 or more carbon atoms. In some embodiments, a radical is branched when it has more than 0.01 mole percent of such side chains. In some embodiments, a radical is branched when it has more than 0.001 mole percent of such side chains.

The terms "radical," "group," "functional group," and "substituent" can be used interchangeably in some contexts and can be used together to further describe a chemical structure. For example, the term "functional group" can refer to a chemical "group" or "radical," which is a chemical structure variable that can be in-chain, pendant and/or terminal to the chemical structure. A functional group may be substituted. Examples of substituents in substituted radicals include, but are not limited to, hydroxyls, alkyls, carboxyls, esters, aminos, amidos, iminos and combinations thereof. Such a functional group can also, for example, contain a heteroatom. Examples of heteroatoms of the hetero-radicals include, but are not limited to, sulfur, phosphorous, oxygen, nitrogen and combinations thereof.

In some embodiments, the functional groups can include, but are not limited to, oxygen-containing groups such as, for example, alcohols, ethers, phenols, and derivatives thereof. Such oxygen-containing groups include, but are not limited to, acetonides, alcohols, alkoxides, bisphenols, carbinols, cresols, diols, enols, enolates, epoxides, ethers, glycols, hydroperoxides, peroxides, phenols, phenolates, phenoxides, pinacols, trioxides, and ynols.

In some embodiments, the functional groups can include, but are not limited to, oxygen-containing groups such as, for example, aldehydes, ketones, quinones and derivatives thereof. Such oxygen-containing groups include, but are not limited to, acetals, acyloins, aldehydes, carbonyl compounds, diosphenols, dypnones, hemiacetals, hemiketals, ketals, ketenes, keto compounds, ketones, quinhydrones, quinomethanes, quinines, and combinations thereof.

In some embodiments, the functional groups can be oxygen-containing groups including, but not limited to, carboxylic acids, oxoacids, sulfonic acids, acid anhydrides, acid thioanhydrides, acyl groups, acyl halides, acylals, anhydrides, carboxylic acids, cyclic acid anhydrides, cyclic anhydrides, esters, fulgides, lactides, lactols, lactones, macrolides, naphthenic acids, ortho acids, ortho esters, oxo carboxylic acids, peroxy acids, and combinations thereof.

In some embodiments, the functional groups can include, but are not limited to, nitrogen-containing groups containing one nitrogen such as, for example, aldimines, aldoximes, alkoxyamines, amic acids, amides, amines, amine oxides, amine ylides, carbamates, hemiaminals, carbonitriles, carboxamides, isocyanides, cyanates, isocyanates, diisocyanates, cyanides, cyanohydrins, diacylamines, enamines, fulminates, hemiaminals, hydroxamic acids, hydroximic acids, hydroxylamines, imides, imidic acids, imidines, imines, oximes, isoureas, ketenimines, ketimines, ketoximes, lactams, lactims, nitriles, nitro, nitroso, nitrosolic acids, oxime O-ethers, quaternary ammonium compounds, quinone imines, quinonoximes, azomethines, ureides, urethanes, and combinations thereof.

In some embodiments, the functional groups can include, but are not limited to, nitrogen-containing groups containing two or more nitrogens such as, for example, aldazines, amide hydrazones, amide oximes, amidines, amidrazones, aminals, amine imides, amine imines, isodiazenes, azans, azides, azo imides, azines, azo compounds, azomethine imides, azoxy compounds, carbodiimides, carboxamidines, diamidides, diazo compounds, diazoamino compounds, diazoates, diazooxides, formamidine disulfides, formazans, hydrazides, hydrazide hydrazones, hydrazide imides, hydrazidines, hydrazines, hydrazo compounds, hydrazones, ketazines, nitramines, nitrile imines, nitrimines, nitrolic acids, nitrosamides, nitrosamines, nitrosimines, ortho amides, semicarbazones, semioxamazones, triazanes, triazenes, and combinations thereof.

In some embodiments, the functional groups can include, but are not limited to, sulfur-containing groups such as sulfones, sulfides, sulfinamides, sulfilimines, sulfimides, sulfinamides, sulfinamidines, sulfines, sulfinic acids, sulfinic anhydrides, sulfinylamines, sulfonamides, sulfones, sulfonediimines, sulfonic acids, sulfonic anhydrides, sulfoxides, sulfoximides, sulphur diimides, thio, thioacetals, thioaldehydes, thioanhydrides, thiocarboxylic acids, thiocyanates, thioether, thiohemiacetals, thioketones, thiol, thiolates, xanthic acids, and combinations thereof.

In some embodiments, the functional groups can include, but are not limited to, silyl groups, halogens, selenoethers, trifluoromethyls, thio-derivatives of urethanes where at least one oxygen atom is replaced by a sulfur atom, phosphoryls, phosphonates, phosphinates, and combinations thereof. In some embodiments, the functional groups are capable of free-radical polymerization and can include, but are not limited to, ethylenically unsaturated groups such as, for example, allyl, vinyl, acryloyl and methacrylol, and maleate and maleimido; and combinations thereof. In some embodiments, the functional groups include halides. In some embodiments, the functional group may include light scattering groups, magnetic groups, nanogold, other proteins, a solid matrix, radiolabels, carbohydrates, and combinations thereof.

The coating may at least substantially promote development of the functional endothelium as the source of the thrombomodulin when compared to a control development of such endothelium formation observed following implantation of a metal or polymer drug-eluting medical device. In some embodiments, the medical device comprises an implant.

It should be appreciated that, in some embodiments, the term "agent" or "drug" can be used interchangeably. An "agent" or "drug" can be a moiety, for example, that may be bioactive, biobeneficial, diagnostic, plasticizing, or have a combination of these characteristics. A "moiety" can be a functional group composed of at least 1 atom, a bonded residue in a macromolecule, an individual unit in a copolymer or an entire polymeric block. It is to be appreciated that any medical articles that can be improved through the teachings described herein are within the scope the invention.

A "bioactive agent" is a moiety that can be combined with a polymer and provides a therapeutic effect, a prophylactic effect, both a therapeutic and a prophylactic effect, or other biologically active effect within a subject. Moreover, the bioactive agents of the present invention may remain linked to a portion of the polymer or be released from the polymer. A "biobeneficial agent" is an agent that can be combined with a polymer and provide a biological benefit within a subject without necessarily being released from the polymer.

A "diagnostic agent" is a type of bioactive agent that can be used, for example, in diagnosing the presence, nature, or extent of a disease or medical condition in a subject. In one embodiment, a diagnostic agent can be any agent that may be used in connection with methods for imaging an internal region of a patient and/or diagnosing the presence or absence of a disease in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, and radiofrequency (RF) and microwave lasers. Diagnostic agents may also include any other agents useful in facilitating diagnosis of a disease or other condition in a patient, whether or not imaging methodology is employed.

Examples of hyaluronic acid derivates include, but are not limited to, sulfated hyaluronic acid such as, for example, O-sulphated or N-sulphated derivatives; esters of hyaluronic acid wherein the esters can be aliphatic, aromatic, arylaliphatic, cycloaliphatic, heterocyclic or a combination thereof; crosslinked esters of hyaluronic acid wherein the crosslinks can be formed with hydroxyl groups of a polysaccharide chain; crosslinked esters of hyaluronic acid wherein the crosslinks can be formed with polyalcohols that are aliphatic, aromatic, arylaliphatic, cycloaliphatic, heterocyclic, or a combination thereof; hemiesters of succinic acid or heavy metal salts thereof; quaternary ammonium salts of hyaluronic acid or derivatives such as, for example, the O-sulphated or N-sulphated derivatives.

Examples of poly(alkylene glycols) include, but are not limited to, PEG, mPEG, poly(ethylene oxide), poly(propylene glycol)(PPG), poly(tetramethylene glycol), and any derivatives, analogs, homologues, congeners, salts, copolymers and combinations thereof. In some embodiments, the poly(alkylene glycol) is PEG. In other embodiments, the poly(alkylene glycol) is mPEG. In other embodiments, the poly(alkylene glycol) is poly(ethylene glycol-co-hydroxybutyrate).

The copolymers that may be used as biobeneficial agents include, but are not limited to, any derivatives, analogs, homologues, congeners, salts, copolymers and combinations of the foregoing examples of agents. Examples of copolymers that may be used as biobeneficial agents in the teachings herein include, but are not limited to, dermatan sulfate, which is a copolymer of D-glucuronic acid or L-iduronic acid and N-acetyl-D-galactosamine; poly(ethylene oxide-co-propylene oxide); copolymers of PEG and hyaluronic acid; copolymers of PEG and heparin; copolymers of PEG and hirudin; graft copolymers of poly(L-lysine) and PEG; copolymers of PEG and a poly(hydroxyalkanoate) such as, for example, poly(ethylene glycol-co-hydroxybutyrate); and any derivatives, analogs, congeners, salts, or combinations thereof. In some embodiments, the copolymer that may be used as a biobeneficial agent can be a copolymer of PEG and hyaluronic acid, a copolymer of PEG and hirudin, and any derivative, analog, congener, salt, copolymer or combination thereof. In other embodiments, the copolymer that may be used as a biobeneficial agent is a copolymer of PEG and a poly(hydroxyalkanoate) such as, for example, poly(hydroxybutyrate); and any derivative, analog, congener, salt, copolymer or combination thereof.

The bioactive agents can be any moiety capable of contributing to a therapeutic effect, a prophylactic effect, both a therapeutic and prophylactic effect, or other biologically active effect in a mammal. The agent can also have diagnostic properties. The bioactive agents include, but are not limited to, small molecules, nucleotides, oligonucleotides, polynucleotides, amino acids, oligopeptides, polypeptides, and proteins. In one example, the bioactive agent inhibits the activity of vascular smooth muscle cells. In another example, the bioactive agent controls migration or proliferation of smooth muscle cells to inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof. It is to be appreciated that one skilled in the art should recognize that some of the groups, subgroups, and individual bioactive agents may not be used in some embodiments of the present invention.

Antiproliferatives include, for example, actinomycin D, actinomycin IV, actinomycin I1, actinomycin X1, actinomycin C1, and dactinomycin (COSMEGEN, Merck & Co., InC). Antineoplastics or antimitotics include, for example, paclitaxel (TAXOL, Bristol-Myers Squibb Co.), docetaxel (TAXOTERE, Aventis S.A.), methotrexate, azathioprine, vincristine, vinblastine, fluorouracil, doxorubicin hydrochloride (ADRIAMYCIN, Pfizer, InC) and mitomycin (MU-TAMYCIN, Bristol-Myers Squibb Co.), and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethyl ketone (synthetic antithrombin), dipyridamole, glycoprotein IIb/IIIa platelet membrane receptor antagonist antibody, recombinant hirudin, and thrombin inhibitors (ANGIOMAX, Biogen, InC), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN and CAPOZIDE, Bristol-Myers Squibb Co.), cilazapril or lisinopril (PRINIVIL and PRINZIDE, Merck & Co., InC); calcium channel blockers such as nifedipine; colchicines; fibroblast growth factor (FGF) antagonists, fish oil (omega 3-fatty acid); histamine antagonists; lovastatin (MEVACOR, Merck & Co., InC); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST, Santen, InC), and any prodrugs, metabolites, analogs, homologues, congeners, derivatives, salts and combinations thereof.

Other bioactive agents useful in the teachings herein include, but are not limited to, free radical scavengers; nitric oxide donors; rapamycin; methyl rapamycin; 42-Epi-(tetrazoylyl) rapamycin (ABT-578); everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs; estradiol; clobetasol; idoxifen; tazarotene; alpha-interferon; host cells such as epithelial cells; genetically engineered epithelial cells; dexamethasone; and any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (4-hydroxy-TEMPO), 2,2',3,4,5,5'-hexamethyl-3-imidazolinium-1-yloxy methyl sulfate, free radical; 4-carboxy-2,2',6,6'-tetramethyl-1-piperinyloxy, free radical (4-carboxy-TEMPO); 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof. The drugs eluted from the coatings taught herein can function as an anti-proliferative or immunosuppressant. In some embodiments, the drug can be rapamycin or a derivative of rapamycin. And, in some embodiments, the drug can be selected from the group consisting of fluoroquinolone, paclitaxel, rapamycin, sirolimus, everolimus, biolimus, zotarolimus, tacrolimus, fibroblast growth factor (bFGF), rapamycin analogs, antisense dexamethasone, angiopeptin, BATIMISTAT, tranilast, transilast, halofuginon, acetylsalicylic acid, hirudin, steroids, ibuprofen, antimicrobials, antibiotics, actinomycin D, tissue plasma activators, and estradiol. One of skill will appreciate that agents that affect vascular smooth muscle cell (VSMC) proliferation or migration can also be used in some embodiments, including, but not limited to transcription factor E2F1.

The agents can be used alone or in combination with other agents to obtain other desired functions of the polymeric compositions. The amounts of the agents that compose the polymeric compositions vary according to a variety of factors including, but not limited to, the biological activity of the agent; the age, body weight, response, or the past medical history of the subject; the type of atherosclerotic disease; the presence of systemic diseases such as, for example, diabetes; the pharmacokinetic and pharmacodynamic effects of the agents or combination of agents; and the design of the compositions for sustained release of the agents. Factors such as these are routinely considered by one of skill in the art when administering an agent to a subject in a desired amount to obtain a desired effect. In some embodiments, the desired amount is termed an "effective amount," where the amount administered elicits a desired response. In some embodiments, the effective amount can be a "therapeutically effective amount", administered in an amount that prevents, inhibits, or ameliorates the symptoms of a disease.

It is to be appreciated that the design of a composition for drug release can be dependent on a variety of factors such as, for example, the therapeutic, prophylactic, ameliorative or diagnostic needs of a patient or condition. In some embodiments, the agent can comprise an antiproliferative and should have a sustained release ranging from about 1 week to about 10 weeks, from about 2 weeks to about 8 weeks, from about 3 weeks to about 7 weeks, from about 4 weeks to about 6 weeks, and any range therein. In some embodiments, the agent can comprise an anti-inflammatory and should have a sustained release ranging from about 6 hours to about 3 weeks, from about 12 hours to about 2 weeks, from about 18 hours to about 10 days, from about 1 day to about 7 days, from about 2 days to about 6 days, or any range therein. In general, the sustained release should range from about 4 hours to about 12 weeks; alternatively, from about 6 hours to about 10 weeks; or from about 1 day to about 8 weeks.

Effective amounts, for example, may be extrapolated from in vitro or animal model systems. In some embodiments, the agent or combination of agents have a concentration that ranges from about 0.001% to about 75%; from about 0.01% to about 70%; from about 0.1% to about 60%; from about 0.25% to about 60%; from about 0.5% to about 50%; from about 0.75% to about 40%; from about 1.0% to about 30%; from about 2% to about 20%; and any range therein, where the percentage is based on the total weight of the polymer and agent or combination of agents.

The terms "plasticizer" and "plasticizing agent" can be used interchangeably in the teachings herein, and refer to any agent, including any agent described above, where the agent can be added to a polymeric composition to modify the mechanical properties of the composition or a product formed from the composition. Plasticizers can be added, for example, to reduce crystallinity, lower the glass-transition temperature (Tg), or reduce the intermolecular forces between polymers, with design goals that may include, but are not limited to, enhancing mobility between polymer chains in the composition. The mechanical properties that are modified include, but are not limited to, Young's modulus, impact resistance (toughness), tensile strength, and tear strength. Impact resistance, or "toughness," is a measure of energy absorbed during fracture of a polymer sample of standard dimensions and geometry when subjected to very rapid impact loading. Toughness can be measured using Charpy and Izod impact tests to assess the brittleness of a material.

A plasticizer can be monomeric, polymeric, co-polymeric, or a combination thereof, and can be combined with a polymeric composition in the same manner as described above for the biobeneficial and bioactive agents. Plasticization and solubility are analogous in the sense that selecting a plasticizer involves considerations similar to selecting a solvent such as, for example, polarity. Furthermore, plasticization can also be provided through covalent bonding by changing the molecular structure of the polymer through copolymerization.

Examples of plasticizing agents include, but are not limited to, low molecular weight polymers such as single-block polymers, multi-block polymers, and copolymers; oligomers such as ethyl-terminated oligomers of lactic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; proteins such as animal proteins and vegetable proteins; oils such as, for example, the vegetable oils and animal oils; silicones; acetylated monoglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, triethylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, triethylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), poly(propylene glycols), and poly(ethylene/propylene glycols); low molecular weight poly(ethylene glycols) such as, for example, PEG 400 and PEG 6000; PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide and dimethyl formamide; sulfoxides such as for example, dimethyl sulfoxide; pyrrolidones such as, for example, n-methylpyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers can be vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid. In other embodiments, the plasticizers can be essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, *cassia* oil, *chenopodium* oil, *chrysanthemum* oil, cinae aetheroleum, citronella oil, lemon oil, citrus oil, costus oil, *curcuma* oil, carlina oil, elemi oil, tarragon oil, *eucalyptus* oil, fennel oil, pine needle oil, pine oil, filicis, aetheroleum, *galbanum* oil, gaultheriae aetheroleum, geranium oil, guaiac wood oil, hazelwort oil, iris oil, *hypericum* oil, calamus oil, camomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, *millefolii* aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, *sassafras* oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

The molecular weights of the plasticizers can vary. In some embodiments, the molecular weights of the plasticizers range from about 10 Daltons to about 50,000 Daltons; from about 25 Daltons to about 25,000 Daltons; from about 50 Daltons to about 10,000 Daltons; from about 100 Daltons to about 5,000 Daltons; from about 200 Daltons to about 2500 Daltons; from about 400 Daltons to about 1250 Daltons; and any range therein. In other embodiments, the molecular weights of the plasticizers range from about 400 Daltons to about 4000 Daltons; from about 300 Daltons to about 3000 Daltons; from about 200 Daltons to about 2000 Daltons; from about 100 Daltons to about 1000 Daltons; from about 50 Daltons to about 5000 Daltons; and any range therein. The molecular weights are taught herein as a number average molecular weight. The amount of plasticizer used in the teachings herein, can range from about 0.001% to about 70%; from about 0.01% to about 60%; from about 0.1% to about 50%; from about 0.1% to about 40%; from about 0.1% to about 30%; from about 0.1% to about 25%; from about 0.1% to about 20%; from about 0.1% to about 10%; from about 0.4% to about 40%; from about 0.6% to about 30%; from about 0.75% to about 25%; from about 1.0% to about 20%; and any range therein, as a weight percentage based on the total weight of the polymer and agent or combination of agents. It should be appreciated that any one or any combination of the plasticizers described above can be used in the teachings herein. For example, the plasticizers can be combined to obtain the desired function. In some embodiments, a secondary plasticizer is combined with a primary plasticizer in an amount that ranges from about 0.001% to about 20%; from about 0.01% to about 15%; from about 0.05% to about 10%; from about 0.75% to about 7.5%; from about 1.0% to about 5%, or any range therein, as a weight percentage based on the total weight of the polymer any agent or combination of agents.

While certain embodiments use gamma irradiation or electron beam (e-beam) sterilization, other types of radiosterilization can be used.

The above described HA-PVA hydrogel provides a natural feel through viscoelastic harmony of properties between the existing tissue and the implant. This can be done by manipulating the viscous component of the implant through flow properties by way of the particle size and particle size distribution ratios. The elastic component is intrinsic within the material tertiary structure (molecular weight and steric hindrance) and cross linking densities. The interpenetrating polymer network hydrogels have a number of desirable properties. These properties include high tensile strength with high water content, making the interpenetrating polymer network hydrogels excellent for use in dermal filling applications. Other advantages and features include: longevity without touch up, hyper-volumic degradation, anatomic compliant and iso-osmotic controlled, among others.

The present invention has been described particularly in connection with a breast, butt, or body implant, among others, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

The methods are applicable to the creation of materials for use in medical, biological and industrial areas including the controlled delivery of agents (which may include proteins, peptides, polysaccharides, genes, DNA, antisense to DNA, ribozymes, hormones, growth factors, a wide range of drugs, imaging agents for CAT, SPECT, x-ray, fluoroscopy, PET, MRI and ultrasound), generation of load bearing implants for hip, spine, knee, elbow, shoulder, wrist, hand, ankle, foot and jaw, generation of a variety of other medical implants and devices (which may include active bandages, transepithelial drug delivery devices, sponges, anti-adhesion materials, artificial vitreous humor, contact lens, breast implants, stents and artificial cartilage that is not load bearing (i.e., ear and nose)), any application where gradients (single or multiple) in mechanical properties or structure are required.

Variations and modifications can, of course, be made without departing from the spirit and scope of the invention. For example, the HA-PVA gel can be used as facial fillers, dermal fillers, butt fillers, breast fillers, and other body part fillers. The implants of the present invention further can be instilled, before or after implantation, with indicated medicines and other chemical or diagnostic agents. Examples of such agents include, but are not limited to, antibiotics, chemotherapies, other cancer therapies, brachy-therapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The present invention has been described particularly in connection with a breast, butt, or body implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement. The other methods, used for characterization of the products according to one embodiment are described in the following examples which illustrate preferred embodiments of one embodiment without, however, being a limitation thereof.

Although the present invention has been described in relation to particular embodiments thereof, many other variations and modifications and other uses will become apparent to those skilled in the art. It is preferred, therefore, that the present invention be limited not by the specific disclosure herein, but only by the appended claims. The other methods, used for characterization of the products according to one embodiment are described in the following examples which illustrate preferred embodiments of one embodiment without, however, being a limitation thereof. Variations and modifications can, of course, be made without departing from the spirit and scope of the invention.

What is claimed is:

1. An apparatus for performing cosmetic enhancements, comprising:
   a processor for performing the cosmetic enhancements;
   a camera for providing body patient data to the processor; and
   an injector controlled by the processor to inject a filler into a patient; wherein the processor
   receives body patient data for a body portion of the patient,
   captures a 3D model of the body portion from the body patient data,
   models shape and size changes in the body portion due to an injected amount of filler,
   iteratively adjusts the shape and size of the model until the patient is satisfied to determine a desired amount of filler to be injected corresponding to a desired shape and size of the body portion, and
   controls the injector to deliver the desired amount of filler in the patient to achieve the desired shape and size of the body portion.

2. The apparatus of claim 1, wherein the injector includes a medicament container, an energy source, and one of: a cannula, a blunt tip, or a needle.

3. The apparatus of claim 1, wherein the processor continuously updates a current shape of a body part, a breast, or a butt from the 3D model of the patient to fit to a desired shape.

4. The apparatus of claim 1, wherein the processor controls the injector to injecting hyaluronic acid (HA), polyvinyl alcohol (PVA), or a combination thereof.

5. The apparatus of claim 1, wherein the processor controls the injector to injecting an anti-inflammatory agent with either hyaluronic acid (HA) or polyvinyl alcohol (PVA) into the patient.

6. The apparatus of claim 1, wherein the processor controls the injector to injecting hyaluronic acid (HA) with polyvinyl alcohol (PVA) to form an HA-PVA hydrogel, and wherein the HA-PVA hydrogel is exposed to an amount of energy effective to crosslink the HA-PVA hydrogel.

7. The apparatus of claim 1, wherein the processor controls the injector to injecting hyaluronic acid (HA) with -2polyvinyl alcohol (PVA) to form an HA-PVA hydrogel; and wherein the HA-PVA hydrogel is exposed to an amount of energy effective to crosslink the HA-PVA hydrogel and to sterilize the HA-PVA hydrogel.

8. The apparatus of claim 1, wherein the processor controls the injector to injecting cross-linked polyvinyl alcohol (PVA) through one or more freeze-thaw cycles.

9. The apparatus of claim 1, wherein the processor controls the injector to injecting polyvinyl alcohol (PVA) cross-linked using e-beam, X-ray, or gamma ray, or beta particle.

10. The apparatus of claim 1, wherein to provide reversibility on-demand, the processor controls the injector to injecting an antihyaluronidase if a prior injection includes HA or a polyvinyl alcohol (PVA) dissolving agent if a prior injection includes PVA.

11. The apparatus of claim 1, wherein the processor controls the injector to injecting a multiply cross-linked material with one or more interpenetrating network (IPN) regions each with one or more single cross-linked extensions radiating out from the IPN.

12. The apparatus of claim 11, wherein the combination of the IPN and the extensions provide one or more of: biodegradation resistance, soft touch feeling, ease of insertion into the human body.

13. The apparatus of claim 1, wherein the processor controls the injector to injecting ciproflaxin uniformly distributed in a hydrogel.

14. The apparatus of claim 1, wherein the processor controls the injector to injecting a drug in a hydrogel that is released at a predetermined timing.

15. The apparatus of claim 14, wherein the processor controls the injector to injecting a compound that reduces implant rejection, transplant rejection, foreign tissue rejection, or capsular contracture.

16. The apparatus of claim 1, wherein the processor controls the injector to injecting hyaluronic acid (HA) or polyvinyl alcohol (PVA) into a dermal area, a face area, a lip area, a breast area, or a buttock area.

17. A method for body augmentation for cosmetics enhancements, comprising:

capturing a 3D model of a patient from body patient data using a camera communicating with a processor;

modelling shape and size changes in a body portion of the patient due to an amount of filler to be placed in the patient using an injector;

iteratively adjusting the shape and size of the model until the patient is satisfied to determine a desired amount of filler to be placed in the patient, corresponding to a desired shape and size of the body portion; and placing, by the processor controlling the injector, the desired amount of filler into the patient in order to achieve the desired shape and size of the body portion.

18. The method of claim 17, comprising:

mixing hyaluronic acid (HA) with polyvinyl alcohol (PVA) to form an HA-PVA hydrogel; and exposing the HA-PVA hydrogel to an amount of energy effective to crosslink the HA and the PVA.

19. The method of claim 17, wherein the exposing comprises e-beaming, X-raying, gamma-raying, beta-raying, or performing one or more freeze-thaw cycles on the HA-PVA hydrogel.

* * * * *